(12) United States Patent
Maillere et al.

(10) Patent No.: US 7,718,575 B2
(45) Date of Patent: May 18, 2010

US007718575B2

(54) METHOD OF SELECTING HLA-DP4 LIGANDS AND THE APPLICATIONS THEREOF

(75) Inventors: Bernard Maillere, Versailles (FR); Florence Castelli, Montrouge (FR); Cécile Buhot, Vitry-sur-Seine (FR); Bertrand Georges, Bauvin (FR)

(73) Assignees: Commissariat a l'Energie Atomique, Paris (FR); Sedac Therapeutics, Loos (FR)

( * ) Notice: Subject to any disclaimer, the term of this patent is extended or adjusted under 35 U.S.C. 154(b) by 914 days.

(21) Appl. No.: 10/491,891

(22) PCT Filed: Oct. 17, 2002

(86) PCT No.: PCT/FR02/03555

§ 371 (c)(1), (2), (4) Date: Oct. 14, 2004

(87) PCT Pub. No.: WO03/040299

PCT Pub. Date: May 15, 2003

(65) Prior Publication Data

US 2005/0059107 A1  Mar. 17, 2005

(30) Foreign Application Priority Data

Oct. 17, 2001  (FR) .................................. 01 13352

(51) Int. Cl.
C40B 20/04 (2006.01)
C07H 21/04 (2006.01)

(52) U.S. Cl. ..................... 506/4; 506/2; 506/7; 506/9; 435/7.24; 435/7.1; 530/300; 530/350

(58) Field of Classification Search .................. 506/4, 506/9, 2, 7; 435/7.24, 7.1; 530/300, 350
See application file for complete search history.

(56) References Cited

U.S. PATENT DOCUMENTS

| | | | | |
|---|---|---|---|---|
| 6,207,391 B1* | 3/2001 | Wu et al. | ........................ | 435/7.1 |
| 6,537,764 B1* | 3/2003 | Gerard et al. | .................... | 435/7.21 |
| 6,815,212 B2* | 11/2004 | Ness et al. | ..................... | 436/173 |
| 7,022,483 B1* | 4/2006 | Albani | .......................... | 435/7.1 |
| 2005/0136402 A1* | 6/2005 | Wang et al. | ..................... | 435/6 |

FOREIGN PATENT DOCUMENTS

| | | | |
|---|---|---|---|
| WO | WO99/18206 | * | 4/1999 |
| WO | WO 2004/014936 A2 | | 2/2004 |
| WO | WO 2006/027468 A2 | | 3/2006 |
| WO | WO 2006/075253 A2 | | 7/2006 |
| WO | WO 2006/082313 A2 | | 8/2006 |
| WO | WO 2007/026078 A2 | | 3/2007 |
| WO | WO 2007/036638 A1 | | 4/2007 |

OTHER PUBLICATIONS

Schultz et al, Cancer Research, 60, 6272-75, (2000).*
Zeng et al, PNAS, 98,7,Mar. 2001, 3964-69.*
Zarour Hassane M et al: "NY-ESO-1 encodes DRB1*0401-restricted epitopes recognized by melanoma-reactive CD4+ T cells." Cancer Research, vol. 60, No. 17, Sep. 1, 2000, pp. 4946-4952, XP002236092, ISSN: 0008-5472, abstract, table 1.
Carballido Jose M et al: "T cell epitope specificity of human allergic and nonallergic subjects to bee venom phospholipase A2." Journal of Immunology, vol. 150, No. 8 Part 1, 1993, pp. 3582-3591, XP002238429, ISSN: 0022-1767, abstract, figure 3.
Falk Kirsten et al: "Pool sequencing of natural HLA-DR, DQ, and DP ligands reveals detailed peptide motifs, constraints of processing, and general rules." Immunogenetics, vol. 39, No. 4, 1994, pp. 230-242, XP008007529, ISSN: 0093-7711, cited in the application, abstract, figure 4.
Marshall Keith W et al: "Role of the polymorphic residues in HLA-DR molecules in allele-specific binding of peptide ligands." Journal of Immunology. vol. 152, No. 10, 1994, pp. 4946-4957, XP002212882, ISSN: 0022-1767, cited in the application, p. 4947, col. 2, paragraph 1.
Castelli Florence A et al: "HLA-DP4, the most frequent HLA II molecule, defines a new supertype of peptide-binding specificity." Journal of Immunology, vol. 169, No. 12, Dec. 15, 2002, pp. 6928-6934, XP002238415, ISSN: 0022-1767, the whole document.
Lee, et al., The Journal of Immunology, "T Cell Recognition of Fibrinogen, A Determinant on the Aα-Chain Does Not Require Processing", vol. 140, No. 4, pp. 1063-1068. Feb. 15, 1988.
Sette, et al., The Journal of Immunology, "Capacity of Intact Proteins to Bind to MHC Class II Molecules", vol. 143, No. 4, pp. 1265-1267. Aug. 15, 1989.
Answers.com Health, printout from http://www.answers.com/topic/high-throughput-screening. pp. 1-5. 2007.
Florence A. Castelli, et al., "HLA-DP4, the Most Frequent HLA II Molecule, Defines a New Supertype of Peptide-Binding Specificity", The Journal of Immunology, 2002, 169:6928-6934.

* cited by examiner

*Primary Examiner*—T. D. Wessendorf
(74) *Attorney, Agent, or Firm*—Oblon, Spivak, McClelland, Maier & Neustadt, L.L.P.

(57) ABSTRACT

A method of selecting a test molecule that binds to HLA-DP4 by (i) incubating HLA-DP4 with the test molecule and a labeled peptide of formula (I) $Z_1X_1X_2X_3X_4X_5X_6X_7X_8X_9Z_2$ thereby forming respective complexes, wherein $Z_1$ and $Z_2$, which may be identical or different, are each either zero or from 1 to 100 amino acids; $X_1$ is an aromatic or hydrophobic amino acid, or S; $X_6$ is an aromatic or hydrophobic amino acid, or C; $X_9$ is an aromatic or hydrophobic amino acid, or C, D, Q, S, T, or E; and $X_2$, $X_3$, $X_4$, $X_5$, $X_7$ and $X_8$ are each an amino acid; (ii) separating the respective complexes formed; (iii) detecting the HLA-DP4/labeled peptide complexes; and (iv) selecting the test molecule that exhibits a binding activity of $IC_{50}<1000$ nM, which corresponds to the concentration of the test molecule that inhibits 50% of the competitive HLA-DP4 binding of the labeled peptide.

12 Claims, 2 Drawing Sheets

SEQUENCE LISTING

<160> NUMBER OF SEQ ID NOS: 134

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Asn Asn Phe Thr Val Ser Phe Trp Leu Arg Val Pro Lys Val Ser
1               5                   10                  15

Ala Ser His Leu Glu
            20

<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Pro Tyr Asn Cys Asp Trp Asp Pro Tyr His Glu Lys Tyr Asp Trp
1               5                   10                  15

Asp Leu Trp Asn Lys Trp Cys Asn
            20

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Phe Leu Leu Thr Arg Ile Leu Thr Ile
1               5                   10

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Val Gln Ile Val Arg Gln Ile Arg Ser Gly Glu Arg Phe Leu Lys
1               5                   10                  15

Ile Trp Ser Gln
            20

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Gly Ile Ser Lys Cys Arg Phe Leu Lys Ile Arg Glu Gly Arg
1               5                   10
```

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Ile Ala Phe Asn Ser Gly Met Glu Pro Gly Val Val Ala Glu Lys Val
1               5                   10                  15
```

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Gly Met Glu Pro Gly Val Val Ala Glu Lys Val Arg Asn Leu Ser Val
1               5                   10                  15
```

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Pro Asn Ala Gln Arg Phe Gly Ile Ser Asn Tyr Cys Gln Ile Tyr Pro
1               5                   10                  15
```

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Thr Gln His Phe Val Gln Glu Asn Tyr Leu Glu Tyr
1               5                   10
```

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Met Trp Ile Thr Gln Cys Phe Leu Pro Val Phe Leu Ala Gln Pro Pro
1               5                   10                  15

Ser Gly Gln Arg
            20
```

<210> SEQ ID NO 11

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Leu Ser Leu Leu Met Trp Ile Thr Gln Cys Phe Leu Pro Val Phe
1               5                   10                  15

Leu Ala Gln Pro Pro
            20

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Glu Leu Trp Trp Val Phe Tyr Ala Gly Asp
1               5                   10

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Pro Gly Ala Pro Ala Asp Val Gln Tyr Asp Leu Tyr Leu Asn Val
1               5                   10                  15

Ala Asn Arg Arg
            20

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Lys Lys Tyr Phe Ala Ala Thr Gln Phe Glu Pro Leu Ala Ala Arg
1               5                   10                  15

Leu

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Lys Tyr Phe Ala Ala Thr Gln Phe Glu Pro Leu Ala Ala Arg Leu
1               5                   10                  15

<210> SEQ ID NO 16
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Lys Lys Tyr Phe Ala Ala Thr Gln Phe Glu Pro Leu
1               5                   10

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Ile Ser Ser Tyr Phe Val Gly Lys Met Tyr Phe Asn Leu Ile Asp
1               5                   10                  15

Thr Lys

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Glu Leu Trp Trp Val Phe Tyr Ala Gly Asp Arg Ala Leu Glu Glu
1               5                   10                  15

Pro His Ala Glu
            20

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Leu Thr Gln His Phe Val Gln Glu Asn Tyr Leu Glu Tyr
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Asn Asn Phe Thr Val Ser Phe Trp Leu Arg Val Pro Lys Val Ser
1               5                   10                  15

Ala

<210> SEQ ID NO 21
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 21

Pro Lys Tyr Val Lys Gln Asn Thr Leu Lys Leu Ala Thr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Tyr Ala Ala Lys Ala Ala Ala Leu Ala Ala
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Val Glu Val Tyr Arg Ala Val Thr Pro Leu Gly Pro Pro Asp
1               5                   10                  15

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Pro Arg Ala Pro Trp Ile Glu Gln Glu Gly Pro Glu Tyr Trp Asp
1               5                   10                  15

Gln Glu

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Lys Lys Tyr Phe Ala Ala Thr Gln Phe Glu
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Lys Lys Tyr Phe Ala Ala Thr Gln Phe Glu Pro
```

-continued

```
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Lys Tyr Phe Ala Ala Thr Gln Phe Glu Pro Leu Ala
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Tyr Phe Ala Ala Thr Gln Phe Glu Pro Leu Ala Ala
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Phe Ala Ala Thr Gln Phe Glu Pro Leu Ala Ala Arg
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Ala Ala Thr Gln Phe Glu Pro Leu Ala Ala Arg Leu
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ala Thr Gln Phe Glu Pro Leu Ala Ala Arg Leu
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 32

Ala Thr Gln Phe Glu Pro Leu Ala Ala Arg Leu
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Tyr Phe Ala Ala Thr Gln Phe Glu Pro Leu Ala Ala Arg Leu
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Lys Lys Tyr Phe Ala Ala Thr Gln Phe Glu Pro Leu Ala Ala
1               5                   10                  15

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Tyr Phe Ala Ala Thr Gln Phe Glu Pro Leu Ala Ala
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Ala Phe Ala Ala Thr Gln Phe Glu Pro Leu Ala Ala
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Tyr Ala Ala Ala Thr Gln Phe Glu Pro Leu Ala Ala
1               5                   10

<210> SEQ ID NO 38

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Tyr Phe Ala Ala Ala Gln Phe Glu Pro Leu Ala Ala
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Tyr Phe Ala Ala Thr Ala Phe Glu Pro Leu Ala Ala
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Tyr Phe Ala Ala Thr Gln Ala Glu Pro Leu Ala Ala
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Tyr Phe Ala Ala Thr Gln Phe Ala Pro Leu Ala Ala
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Tyr Phe Ala Ala Thr Gln Phe Glu Ala Leu Ala Ala
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43
```

Lys Tyr Phe Ala Ala Thr Gln Phe Glu Pro Ala Ala Ala
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Lys Phe Ala Ala Thr Gln Phe Glu Pro Leu Ala Ala
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Tyr Lys Ala Ala Thr Gln Phe Glu Pro Leu Ala Ala
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Tyr Phe Lys Ala Thr Gln Phe Glu Pro Leu Ala Ala
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Tyr Phe Ala Lys Thr Gln Phe Glu Pro Leu Ala Ala
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Lys Tyr Phe Ala Ala Lys Gln Phe Glu Pro Leu Ala Ala
1               5                   10

<210> SEQ ID NO 49
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 49

Lys Tyr Phe Ala Ala Thr Lys Phe Glu Pro Leu Ala Ala
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Tyr Phe Ala Ala Thr Gln Lys Glu Pro Leu Ala Ala
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Tyr Phe Ala Ala Thr Gln Phe Lys Pro Leu Ala Ala
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Tyr Phe Ala Ala Thr Gln Phe Glu Lys Leu Ala Ala
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Tyr Phe Ala Ala Thr Gln Phe Glu Pro Lys Ala Ala
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Tyr Phe Ala Ala Thr Gln Phe Glu Pro Leu Lys Ala
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Tyr Phe Ala Ala Thr Gln Phe Glu Pro Leu Ala Lys
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Tyr Tyr Ala Ala Thr Gln Phe Glu Pro Leu Ala Ala
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Tyr Leu Ala Ala Thr Gln Phe Glu Pro Leu Ala Ala
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Tyr Glu Ala Ala Thr Gln Phe Glu Pro Leu Ala Ala
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Tyr Asn Ala Ala Thr Gln Phe Glu Pro Leu Ala Ala
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Tyr Thr Ala Ala Thr Gln Phe Glu Pro Leu Ala Ala
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Tyr Phe Ala Ala Phe Gln Phe Glu Pro Leu Ala Ala
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Tyr Phe Ala Ala Leu Gln Phe Glu Pro Leu Ala Ala
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Tyr Phe Ala Ala Glu Gln Phe Glu Pro Leu Ala Ala
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Tyr Phe Ala Ala Asp Gln Phe Glu Pro Leu Ala Ala
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys Tyr Phe Ala Ala Asn Gln Phe Glu Pro Leu Ala Ala
1               5                   10

<210> SEQ ID NO 66
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 66

Lys Tyr Phe Ala Ala Tyr Gln Phe Glu Pro Leu Ala Ala
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Tyr Phe Ala Ala Arg Gln Phe Glu Pro Leu Ala Ala
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Tyr Phe Ala Ala Ser Gln Phe Glu Pro Leu Ala Ala
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Tyr Phe Ala Ala Thr Gln Tyr Glu Pro Leu Ala Ala
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Tyr Phe Ala Ala Thr Gln Leu Glu Pro Leu Ala Ala
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Tyr Phe Ala Ala Thr Gln Trp Glu Pro Leu Ala Ala
1               5                   10
```

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Tyr Phe Ala Ala Thr Gln Glu Glu Pro Leu Ala Ala
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Tyr Phe Ala Ala Thr Gln Asn Glu Pro Leu Ala Ala
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Lys Tyr Phe Ala Ala Thr Gln Thr Glu Pro Leu Ala Ala
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys Tyr Phe Ala Ala Thr Gln Phe Glu Pro Phe Ala Ala
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Tyr Phe Ala Ala Thr Gln Phe Glu Pro Tyr Ala Ala
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 77

Lys Tyr Phe Ala Ala Thr Gln Phe Glu Pro Glu Ala Ala
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Tyr Phe Ala Ala Thr Gln Phe Glu Pro Asp Ala Ala
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Lys Tyr Phe Ala Ala Thr Gln Phe Glu Pro Asn Ala Ala
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Lys Tyr Phe Ala Ala Thr Gln Phe Glu Pro Arg Ala Ala
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Lys Tyr Phe Ala Ala Thr Gln Phe Glu Pro Val Ala Ala
1               5                   10

<210> SEQ ID NO 82
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Leu Met Trp Ile Thr Gln Cys Phe Leu Pro Val Phe Leu Ala Gln
1               5                   10                  15

Pro Pro Ser Gly Gln Arg Arg
            20
```

```
<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Pro Gly Val Leu Leu Lys Glu Phe Thr Val Ser Gly Asn Ile Leu Thr
1               5                   10                  15

Ile Arg Leu Thr Ala Ala Asp His Arg
            20                  25

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Lys Phe Tyr Asp Cys Leu Lys Asn Ser Ala Asp Thr Ser Ser Tyr
1               5                   10                  15

Phe

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Tyr Phe Val Gly Lys Met Tyr Phe Asn Leu Ile Asp Thr Lys Cys Tyr
1               5                   10                  15

Lys Leu

<210> SEQ ID NO 87
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Asn Gly Tyr Arg Ala Leu Met Asp Lys Ser Leu His Val Gly Thr
1               5                   10                  15
```

Gln Cys Ala Leu Thr Arg Arg
            20

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Cys Leu Lys Asn Ser Ala Asp Thr Ile Ser Ser Tyr Phe Val Gly
1               5                   10                  15

Lys Met

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asn Ser Ala Asp Thr Ile Ser Ser Tyr Phe Val Gly Lys Met Tyr Phe
1               5                   10                  15

Asn Leu

<210> SEQ ID NO 90
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Met Pro Arg Glu Asp Ala His Phe Ile Tyr Gly Tyr Pro Lys Lys Gly
1               5                   10                  15

His Gly His Ser
            20

<210> SEQ ID NO 91
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Leu Leu Ile Gly Cys Trp Tyr Cys Arg Arg Arg Asn Gly Tyr Arg Ala
1               5                   10                  15

Leu Met Asp Lys
            20

<210> SEQ ID NO 92
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

-continued

Leu Met Asp Lys Ser Leu His Val Gly Thr Gln Cys Ala Leu Thr Arg
1               5                   10                  15

Arg Cys Pro Gln
            20

<210> SEQ ID NO 93
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Tyr Glu Lys Leu Ser Ala Glu Gln Ser Pro Pro Tyr Ser Pro
1               5                   10                  15

<210> SEQ ID NO 94
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Phe Leu Pro Val Phe Leu Ala Gln Pro Pro Ser Gly Gln Arg Arg
1               5                   10                  15

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Lys Tyr Asp Ala Ala Thr Gln Phe Glu Pro Leu Ala Ala
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Tyr Gly Ala Ala Thr Gln Phe Glu Pro Leu Ala Ala
1               5                   10

-continued

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Lys Tyr His Ala Ala Thr Gln Phe Glu Pro Leu Ala Ala
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Tyr Ile Ala Ala Thr Gln Phe Glu Pro Leu Ala Ala
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Lys Tyr Met Ala Ala Thr Gln Phe Glu Pro Leu Ala Ala
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Lys Tyr Pro Ala Ala Thr Gln Phe Glu Pro Leu Ala Ala
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Lys Tyr Gln Ala Ala Thr Gln Phe Glu Pro Leu Ala Ala
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 103

Lys Tyr Arg Ala Ala Thr Gln Phe Glu Pro Leu Ala Ala
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Lys Tyr Ser Ala Ala Thr Gln Phe Glu Pro Leu Ala Ala
1               5                   10

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Lys Tyr Val Ala Ala Thr Gln Phe Glu Pro Leu Ala Ala
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Lys Tyr Trp Ala Ala Thr Gln Phe Glu Pro Leu Ala Ala
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Lys Tyr Phe Ala Ala Gly Gln Phe Glu Pro Leu Ala Ala
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Lys Tyr Phe Ala Ala Pro Gln Phe Glu Pro Leu Ala Ala
1               5                   10

<210> SEQ ID NO 109
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Lys Tyr Phe Ala Ala His Gln Phe Glu Pro Leu Ala Ala
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Lys Tyr Phe Ala Ala Thr Gln Asp Glu Pro Leu Ala Ala
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Lys Tyr Phe Ala Ala Thr Gln Gly Glu Pro Leu Ala Ala
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Lys Tyr Phe Ala Ala Thr Gln His Glu Pro Leu Ala Ala
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Lys Tyr Phe Ala Ala Thr Gln Ile Glu Pro Leu Ala Ala
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Lys Tyr Phe Ala Ala Thr Gln Met Glu Pro Leu Ala Ala
```

```
1               5                   10
```

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

```
Lys Tyr Phe Ala Ala Thr Gln Pro Glu Pro Leu Ala Ala
1               5                   10
```

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

```
Lys Tyr Phe Ala Ala Thr Gln Gln Glu Pro Leu Ala Ala
1               5                   10
```

<210> SEQ ID NO 117
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Lys Tyr Phe Ala Ala Thr Gln Arg Glu Pro Leu Ala Ala
1               5                   10
```

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

```
Lys Tyr Phe Ala Ala Thr Gln Ser Glu Pro Leu Ala Ala
1               5                   10
```

<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

```
Lys Tyr Phe Ala Ala Thr Gln Val Glu Pro Leu Ala Ala
1               5                   10
```

<210> SEQ ID NO 120
<211> LENGTH: 13
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 120

Lys Tyr Phe Ala Ala Thr Gln Trp Glu Pro Leu Ala Ala
1               5                   10

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Lys Tyr Phe Ala Ala Thr Gln Cys Glu Pro Leu Ala Ala
1               5                   10

<210> SEQ ID NO 122
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Lys Tyr Phe Ala Ala Thr Gln Phe Glu Pro Gly Ala Ala
1               5                   10

<210> SEQ ID NO 123
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Lys Tyr Phe Ala Ala Thr Gln Phe Glu Pro His Ala Ala
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Lys Tyr Phe Ala Ala Thr Gln Phe Glu Pro Ile Ala Ala
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Lys Tyr Phe Ala Ala Thr Gln Phe Glu Pro Pro Ala Ala
1               5                   10

<210> SEQ ID NO 126
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Lys Tyr Phe Ala Ala Thr Gln Phe Glu Pro Gln Ala Ala
1               5                   10

<210> SEQ ID NO 127
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Lys Tyr Phe Ala Ala Thr Gln Phe Glu Pro Ser Ala Ala
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Lys Tyr Phe Ala Ala Thr Gln Phe Glu Pro Thr Ala Ala
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Lys Tyr Phe Ala Ala Thr Gln Phe Glu Pro Trp Ala Ala
1               5                   10

<210> SEQ ID NO 130
<211> LENGTH: 4
<212> TYPE: PRT
<213> ORGANISM: Homo sapiens

<400> SEQUENCE: 130

Gly Gly Pro Met
1

<210> SEQ ID NO 131
<211> LENGTH: 4
<212> TYPE: PRT
<213> ORGANISM: Homo sapiens

<400> SEQUENCE: 131

Asp Glu Ala Val
1

<210> SEQ ID NO 132
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Trp Ile Thr Gln Cys Phe Leu Pro Val
1               5

<210> SEQ ID NO 133
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asp Lys Phe Tyr Asp Cys Leu Lys Asn Ser Ala Asp Thr Ile Ser Ser
1               5                   10                  15

Tyr Phe

<210> SEQ ID NO 134
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Arg Arg Asn Gly Tyr Arg Ala Leu Met Asp Lys Ser Leu His Val Gly
1               5                   10                  15

Thr Gln Cys Ala Leu Thr Arg Arg
            20
```

METHOD OF SELECTING HLA-DP4 LIGANDS AND THE APPLICATIONS THEREOF

Cross-Reference to Related Applications

Figure 1:
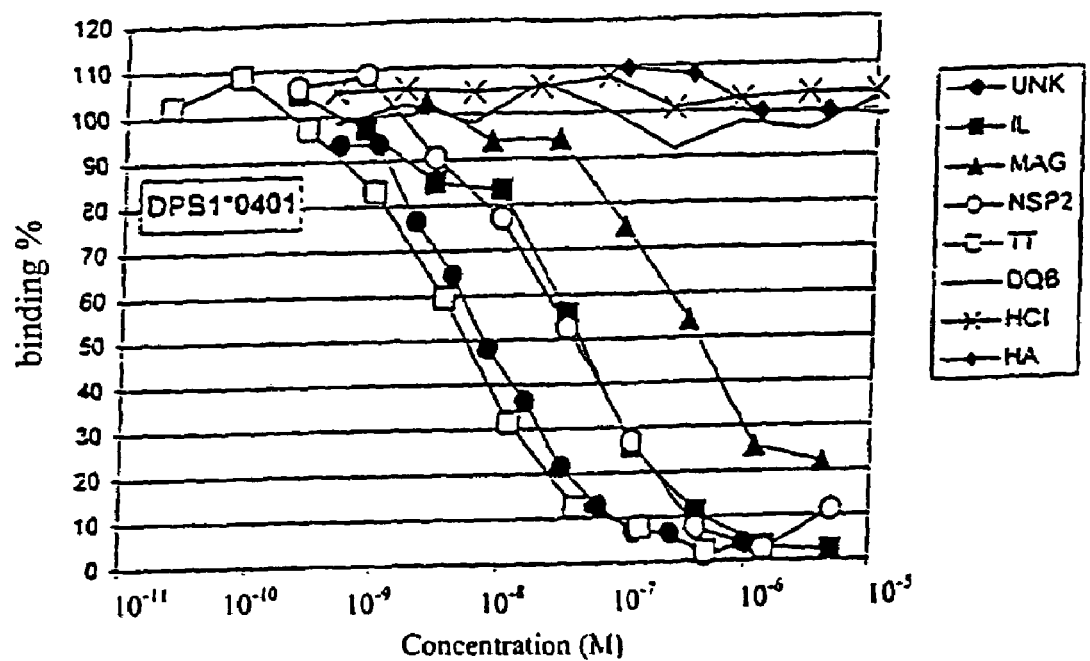
Figure 1:
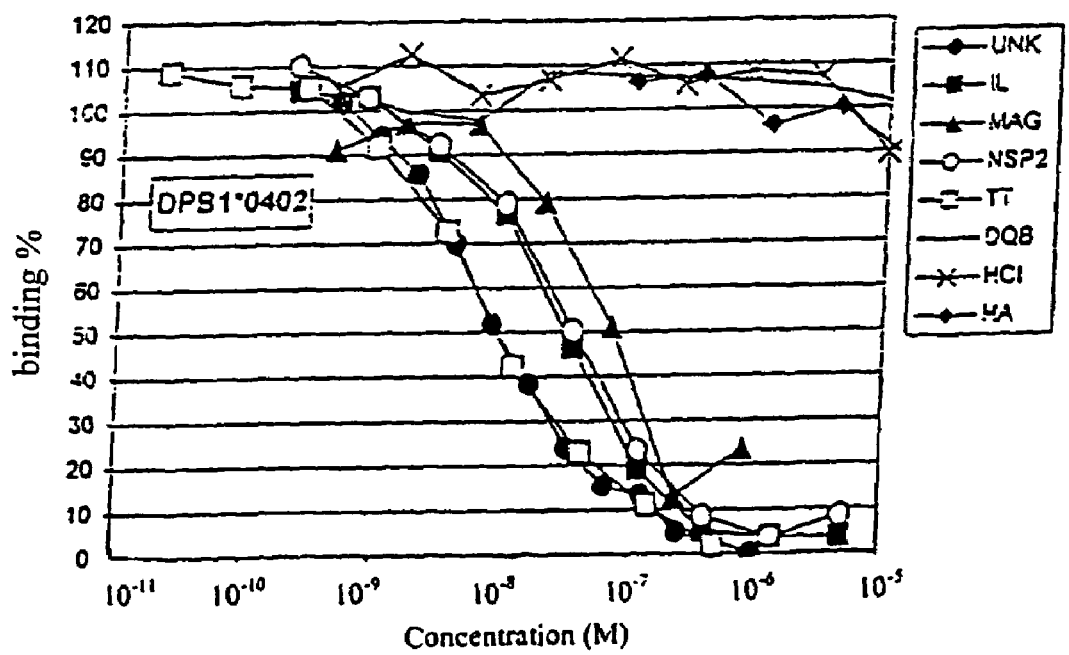

The present application is a 35 U.S.C. §371 National Stage patent application of International patent application PCT/FR02/03555, filed on Oct. 17, 2002, which claims priority to French patent application 01/13352, filed on Oct. 17, 2001.

The present invention relates to a method of selecting HLA-DP4 ligands and to the applications thereof.

CD4+ T lymphocytes are among the main cells which regulate the immune response. They are antigen-specific and are in fact capable of recognizing the presence of a pathogenic agent, of an allergen or of a tumor cell, and of triggering an immune response. Recognition of these antigens in fact results in the activation of the CD4+ T lymphocytes, which secrete most of the cytokines necessary for the recruitment of effector cells, namely cytotoxic CD8+ lymphocytes and antibody-producing B lymphocytes. CD4+ T lymphocytes are also involved in the activation of cells by cell contacts and, for example induce the activation, via the CD40 molecule, of antigen-presenting dendritic cells. CD4+ T lymphocyte activation is a favorable prognostic in infections with viruses such as the human immunodeficiency virus (HIV), human papilloma viruses (HPVs) or the hepatitis C virus (HCV), and these cells appear to be necessary for antitumor immunity. Their role is not, however, systematically beneficial for the organism. Autoimmune diseases very commonly result from uncontrolled activation of CD4+ T lymphocytes. This is the case of multiple sclerosis and of insulin-dependent diabetes. These lymphocytes also participate in the establishment of allergic diseases. IL4, which is mainly secreted by CD4+ T lymphocytes, is in fact the main factor which results in the production of IgE. Finally, the role of CD4+ T lymphocytes in the triggering of transplant rejection is well established. Thus, depending on the disease, treatments are aimed at triggering the activation of CD4+ T lymphocytes (immunization against a pathogenic agent or a tumor cell) or at decreasing the state of activation of CD4+ T lymphocytes (desensibilization against the allergy, prevention of transplant rejection).

The activation of CD4+ T lymphocytes takes place under the effect of the presentation of antigenic peptides by the molecules of the major histocompatibility complex type II borne by the antigen-presenting cells (APCs); in humans, they are called HLA II molecules for human leukocyte Antigen type II. These antigenic peptides, called T epitopes, result from the proteolytic degradation of the antigens by the antigen-presenting cells. They are variable in length, generally from 13 to 25 amino acids, and have a sequence which makes them capable of binding to the HLA II molecules. It is well known that, just like the native antigen, a T-epitope peptide is capable of stimulating, in vitro, CD4+ T lymphocytes which are specific for them, or of recruiting them in vivo. It is therefore sufficient to induce a CD4+ T response. Interestingly, it is also known that, according to the modes of presentation (route of administration, doses, possible addition of an adjuvant), the recognition of these peptides leads either to activation of the CD4+ T lymphocytes (ALEXANDER et al., *J. Immunol.*, 2000, 164, 1625-1633; DEL GUERCIO et al., *Vaccine*, 1997, 15, 441-448; FRANKE et al., *Vaccine*, 1999, 17, 1201-1205), or to anergy thereof (MULLER et al., *J. Allergy Clin. Immunol.*, 1998, 101, 747-754; OLDFIELD et al., *J. Immunol.*, 2001, 167, 1734-1739). These T-epitope peptides are therefore capable both of contributing to the composition of a vaccine or of serving to decrease the undesired activation of CD4+ T lymphocytes. They are also capable of contributing to a test for diagnosing the immune state of patients or of normal individuals, based on the direct detection (lymphocyte proliferation assay) or indirect detection (production of antibodies, of cytokines, etc.) of said activated CD4+ T lymphocytes.

One of the major problems which limits the use of these peptides is the identification of these epitopes, given that their sequence varies from one individual to another due to the polymorphism of the HLA II molecules. In fact, the HLA II molecules are hetero dimers consisting of an alpha (α)-chain and of a beta (β)-chain which are polymorphic. Four types of HLA II molecules exist per individual (2 HLA-DR, 1 HLA-DQ and 1 HLA-DP). The HLA-DR molecule, the beta (β)-chain of which is encoded by the DRB1 gene, is the most commonly expressed. To date, the beta-chain encoded by the DRB1 gene is the most polymorphic and has 273 alleles. For the HLA-DQ and HLA-DP molecules, the two chains (α and β) of which they are formed are polymorphic but they have fewer alleles. There are in fact 21 DQA1 alleles (α-chain of HLA-DQ), 45 DQB1 alleles (β-chain of HLA-DQ), 19 DPA1 alleles (α-chain of HLA-DP) and 93 DPB1 alleles (β-chain of HLA-DP). However, combination between the two α- and β-chains encoded by these alleles gives rise to many HLA-DQ and HLA-DP molecules. Because of this polymorphism, these isoforms possess binding properties which are different from one another, which implies that they can bind different peptides of the same antigen. Thus, each individual recognizes in an antigen a set of peptides, the nature of which depends on the HLA II molecules which characterizes said individual. Since a large number of HLA II alleles exists, it may be assumed that there exists, in a given sequence, a considerable repertoire of T-epitope peptides having very different sequences, each one specific for a different allele.

However, this HLA II molecule diversity is not as great on the scale of each population as on a worldwide scale, as illustrated by table I below.

TABLE I

Gene frequencies for the HLA class II molecules that are most abundant in the Caucasian population (Europe, USA)*, according to J. Colombani, 1993, HLA: immune functions and medical applications, published by John Libbey Eurotext.

| Molecules | α-chain | Frequency (%) | β-chain | Frequency (%) | Abundant molecules |
|---|---|---|---|---|---|
| HLA-DR | DRA*0101 | 100 | DRB1*0101 | 9.3 | DRA*0101/DRB1*0101 |
| | | | DRB1*1501 | 8.0 | DRA*0101/DRB1*1501 |
| | | | DRB1*0301 | 10.9 | DPA*0101/DRB1*0301 |
| | | | DRB1*0401 | 5.6 | DRA*0101/DRB1*0401 |
| | | | DRB1*1101 | 9.2 | DRA*0101/DRB1*1101 |
| | | | DRB1*1301 | 6.0 | DRA*0101/DRB1*1301 |
| | | | DRB1*0701 | 14.0 | DRA*0101/DRB1*0701 |

TABLE I-continued

Gene frequencies for the HLA class II molecules that are most abundant in the Caucasian population (Europe, USA)*, according to J. Colombani, 1993, HLA: immune functions and medical applications, published by John Libbey Eurotext.

| Molecules | α-chain | Frequency (%) | β-chain | Frequency (%) | Abundant molecules |
|---|---|---|---|---|---|
| | | | DRB3*0101 | 9.2 | DRA*0101/DRB3*0101 |
| | | | DRB3*0202 | 12.0 | DRA*0101/DRB1*0202 |
| | | | DRB4*0101 | 28.4 | DRA*0101/DRB4*0101 |
| | | | DRB5*0101 | 7.9 | DRA*0101/DRB5*0101 |
| HLA-DQ | DQA1*0101 | 17.0 | DQB1*0501 | 14.9 | DQA1*0101/DQB1*0501 |
| | DQA1*0102 | 15.8 | DQB1*0602 | 9.8 | DQA1*0501/DQB1*0301 |
| | DQA1*0201 | 12.4 | DQB1*0603 | 5.8 | DQA1*0501/DQB1*0201 |
| | DQA1*0301 | 14.5 | DQB1*0201 | 21.3 | DQA1*0301/DQB1*0302 |
| | DQA1*0501 | 20.9 | DQB1*0301 | 12.0 | DQA1*0102/DQB1*0602 |
| | | | DQB1*0302 | 13.0 | DQA1*0201/DQB1*0201 |
| HLA-DP | **DPA1*0103 | 78.2** | DPB1*0101 | 7.1 | DPA1*0201/DPB1*0101 |
| | DPA1*0201 | 21.2 | DPB1*0201 | 11.9 | DPA1*0103/DPB1*0201 |
| | | | DPB1*0301 | 9.1 | DPA1*0103/DPB1*0301 |
| | | | **DPB1*0401** | 40.1 | **DPA1*0103/DPB1*0401** |
| | | | **DPB1*0402** | 11.0 | **DPA1*0103/DPB1*0402** |

*The gene frequencies for the 2 HLA-DP4 molecules are indicated in bold.

Thus, for the HLA-DR and HLA-DQ molecules, about ten alleles are sufficient to cover more than 60% of the gene frequency found in the Caucasian population and therefore to involve more than 85% of the Caucasian population.

For the HLA-DP molecules, the most common molecule is the DP4 molecule derived from the DPA1*0103 and DPB1*0401 alleles, which have gene frequencies of 78.2% and 40%, respectively. Three other DP molecules have frequencies which exceed 5%: a DP3 molecule (DPA1*0103/DPB1*0301), a DP2 molecule (DPA1*0103/DPB1*0201) and a DP4 molecule (DPA1*0103/DPB1*0402); the HLA II molecules are named as a function of the DPB1 allele encoding the β-chain which is the most polymorphic.

Thus, four HLA-DP molecules (1 DP3 molecule, 1 DP2 molecule and 2 DP4 molecules) are therefore sufficient to cover 71% of the gene frequency of the Caucasian population, the two DP4 molecules covering 51% by themselves. Each of these DP4 molecules comprises a variable α-chain encoded either by DPA1*0103, which is the most common (78.2%), or by DPA1*0201 (20.2%), the two α-chains differing only at the level of 3 amino acids (positions 31, 50 and 83; table II). The HLA-DP4 molecules which exhibit a high allelic frequency in the Caucasian population (of the order of 50% in Europe and 80% in North America) are also present at not insignificant frequencies in the other populations (allelic frequency of the order of 60% in South America, 60% in India, 25% in Africa and 15% in Japan, Colombani et al., mentioned above).

TABLE II

Polymorphism of the α- and β-chains (SEQ ID NOS: 130, 131, 131 and 131, respectively, in order of appearance) of the HLA-DP molecules in the Caucasian population (Europe, USA), according to J. Colombani, mentioned above.

| Alleles | Freq (%) | Polymorphic positions* | | | | | | | | | | | | | |
|---|---|---|---|---|---|---|---|---|---|---|---|---|---|---|---|
| | | β-chain | | | | | | | | | | | | | |
| | | 8 | 9 | 11 | 37 | 38 | 57 | 58 | 59 | 67 | 71 | 78 | 86 | 87 | 88 | 89 |
| 401 | 40.1 | L | F | G | F | A | A | A | E | I | K | M | G | G | P | M |
| 402 | 11.0 | — | — | — | — | V | D | E | — | — | — | — | — | — | — | — |
| 201 | 11.9 | — | — | — | — | V | D | E | — | — | E | — | — | — | — | — |
| 501 | 1.3 | — | — | — | L | V | E | — | — | — | — | — | D | — | — | — |
| 101 | 7.1 | V | Y | G | Y | — | — | — | — | — | — | — | D | E | A | V |
| 301 | 9.1 | V | Y | L | — | V | D | E | D | L | — | V | D | E | A | V |
| 901 | 1.1 | V | H | L | — | V | D | E | D | I | E | V | D | E | A | V |

| | | α-chain | | |
|---|---|---|---|---|
| | | 31 | 50 | 83 |
| 103 | 78.2 | M | Q | T |
| 201 | 21.2 | Q | R | A |

*The sequences, available on the internet site http://www.ebi.ac.uk/imgt/hla, are numbered according to the numbering of STERN et al. (Nature, 1994, 368, 215-221) for the HLA-DR molecule; as the residues at positions 23 and 24 are absent in the DPB sequences, the residues indicated at positions 37, 38, 57, 59, 67, 71, 78, 86, 87, 88 and 89 correspond respectively to positions 35, 36, 55, 56, 57, 65, 69, 76, 84, 85 and 87 in the DPB sequence.

However, despite the high frequencies, each of these DP4 molecules has only been very partially studied; the most common studies in fact result from the isolation of HLA-DP4 molecule-restricted CD4+ T lymphocyte clones specific for the peptides given in table III below, derived from the following antigens:

Antigens from pathogenic microorganisms, such as the tetanus toxin (WYSS CORAY et al., *Eur J. Immunol.*, 1992, 22, 2295), the *Blastomyces dermatitidis* WI-1 antigen (CHANG et al., *Inf. Immun.*, 2000, 68, 502), the *Mycobacterium bovis* hsp 65 protein (GASTON et al., *Int. Immunol.*, 1991, 3, 965-972), the hepatitis B virus S antigen (HBsAg; CELIS et al., *J. Virol.*, 1989, 63, 747), the rabies virus non-structural phosphoprotein (RV-NS) or influenza B virus neuraminidase (IBV-Nm; CELIS et al., *J. Immunol.*, 1990, 145, 305) and the herpes simplex virus type 1 UL21 protein (KOELLE et al., *J. Virol.*, 2000, 74, 10930-10938), allergens such as the major allergen of Dermatophagoides pteronyssinus (HIGGINS, *J. Allergy Clin. Immunol.*, 1992, 90, 749), and tumor antigens such as MAGE-A3 (SCHULTZ et al., *Cancer Res.*, 2000, 60, 6272) and NY-ESO1 (ZENG et al., *P.N.A.S.*, 2001, 98, 3964-3969).

system of the patients during natural infection with an antigen; these epitopes are not necessarily the most effective for inducing an immune response against this same antigen.

Using another approach, namely the analysis of four peptides naturally present on DP4 molecules [peptide 127-146 of the α-chain of the IL3 receptor (IL3 127-146; SEQ ID NO: 13) and three peptides of unknown origin: UNK1 (SEQ ID NO:14), UNK2 (SEQ ID NO:15) and UNK3 (SEQ ID NO:16); table III], FALK et al. (*Immunogenetics*, 1994, 39, 230-242) have proposed a DP4 molecule-binding consensus sequence. This sequence comprises three anchoring residues, respectively at positions P1, P7 and P9/P10. P1 and P7 are hydrophobic or aromatic (Y, V, L, F, I, A, M, W) and P9/P10 are preferably aliphatic; however, a Y residue is tolerated at positions P9/P10, but not an F residue. The residues P1 and P7 are preceded by groups of charged residues (K, R, E, N, Q for P1 and N, K, E for P7), and small residues (A, V) are common at position P3 and position P9. Table III shows that the only other DP4-ligand peptides exhibiting this unit are the overlapping peptides NY-ESO1 161-180 and NY-ESO1 156-175. Consequently this unit proposed by FALK et al. does not make it possible to define a DP4 molecule-binding unit shared by all the peptides that are ligands for the DP4 molecules, identified by functional assays.

TABLE III

Sequences of the peptides which are ligands for the HLA-DP4 molecules

| Peptides | Sequences | Identification number | Reference |
|---|---|---|---|
| TT947-967 | FNNFTVSFWLRVPKVSASHLE | SEQ ID NO: 1 | Wyss Coray et al., 1992 |
| PSN 265 | DPYNCDWDPYHEKYDWDLWNKWCN | SEQ ID NO: 2 | Chang et al., 2000 |
| S1d (HBsAg 19-28) | FFLLTRILTI | SEQ ID NO: 3 | Celis et al., 1989 |
| NS-p2 (RV NS 101-120) | GVQIVRQIRSGERFLKIWSQ | SEQ ID NO: 4 | Celis et al. 1990 |
| FLU-p1 (IBV Nm 247-260) | GISKCRFLKIREGR | SEQ ID NO: 5 | Celis et al., 1990 |
| MT451-466 | IAFNSGMEPGVVAEKV | SEQ ID NO: 6 | Gaston et al., 1991 |
| MT456-471 | GMEPGVVAEKVRNLSV | SEQ ID NO: 7 | Gaston et al., 1991 |
| Derp 101-119 | PNAQRFGISNYCQIYP | SEQ ID NO: 8 | Higgins, 1992 |
| MAG 247-258 | TQHFVQENYLEY | SEQ ID NO: 9 | Schultz et al., 2000 |
| NY-ESO1 161-180 | MWITQCFLPVFLAQPPSGQR | SEQ ID NO: 10 | Zeng et al., 2001 |
| NY-ESO1 156-175 | QLSLLMWITQCFLPVFLAQPP | SEQ ID NO: 11 | Zeng et al., 2001 |
| UL21 283-293 | RELWWVFYAGD | SEQ ID NO: 12 | Koelle et al., 2000 |
| IL3 127-146 | GPGAPADVQYDLYLNVANRR | SEQ ID NO: 13 | Falk et al., 1994 |
| UNK1 (UNK 1-17) | EKKYFAATQFEPLAARL | SEQ ID NO: 14 | Falk et al., 1994 |
| UNK2 (UNK 2-17) | KKYFAATQFEPLAARL | SEQ ID NO: 15 | Falk et al., 1994 |
| UNK3 (UNK 1-13) | EKKYFAATQFEPL | SEQ ID NO: 16 | Falk et al., 1994 |

The abovementioned studies which are based on the isolation of HLA-DP4 molecule-restricted CD4+ T lymphocyte clones use a functional assay (proliferation assay) which has not made it possible to demonstrate a DP4 molecule-binding unit shared by all these peptides. In addition, this assay is very laborious to implement due to the fact that it requires a large number of correctly sampled patients, so that they represent the diversity of HLA II molecules of the entire population. In addition, the epitopes defined are those used by the immune system Although DP9 molecule-binding assays (DONG et al., *J. Immunol.* 1995, 154, 4536-4545) and DP2 molecule-binding assays (CHICZ et al., *J. Immunol.*, 1997, 159, 4935-4942), derived from those developed from the DR molecules [MARSHALL et al., *J. Immunol.*, 1994, 152, 4946 (HLA-DR1); patent FR 99 0879 and TEXIER et al., *J. Immunol.*, 2000, 164, 3177 (HLA-DR1, -DR2, -DR3, -DR4, -DR7, -DR11 and -DR13)] make it possible to isolate peptides specific for, respectively, DP9 and DP2, these assays do not make it possible to isolate peptides specific for DP4 (CHICZ et al., mentioned above): the peptides isolated using the DP2-binding assay have a high affinity for DP2 (binding activity<10 nM), whereas peptides known to be DP4-restricted, such as the HBsAg 14-33 peptide, exhibit moderate activity (20 µM).

In addition, due to the considerable differences in the residues of the binding site, between the principal DP molecules, the binding assays developed for these molecules do not make it possible to identify DP4-restricted peptides.

Thus, the binding units shared by all the peptides capable of binding to HLA-DP4 molecules have not been identified, in particular due to the fact that there is no method of identifying such peptides which is simple to implement and suitable for the simultaneous screening of a large number of peptides, such as banks of overlapping peptides representing the antigen sequence of interest.

Nevertheless, given the frequency of the DP4 molecules, the peptides which bind to the DP4 molecules constitute candidate peptides for specific immunotherapy and immunization and could be used for diagnosing the immune state of patients or of normal individuals.

The inventors have therefore developed a method of selecting HLA-DP4 ligands, which has enabled them to isolate HLA-DP4-specific ligands, in particular peptides, and to specify the binding units shared by the HLA-DP4-ligand peptides, based on the peptides obtained.

Consequently, a subject of the present invention is a method of selecting HLA-DP4-ligand molecules, comprising the following steps:

(i) incubation of purified HLA-DP4 with a tracer consisting of a prelabeled peptide and able to be detected by an appropriate signal, which tracer peptide is chosen from the group consisting of the peptides exhibiting a signal/background noise ratio greater than 5, at a concentration of 10 nM, in a direct HLA-DP4-binding assay, and corresponding to general formula (I) $Z_1X_1X_2X_3X_4X_5X_6X_7X_8X_9Z_2$ in which:

$Z_1$ and $Z_2$, which may be identical or different, are zero or each represent a peptide of 1 to 100 natural or synthetic amino acids, preferably of 1 to 30 amino acids, even more preferably of 1 to 10 amino acids;

$X_6$ represents an aromatic or hydrophobic amino acid, or a cysteine (C);

$X_1$ represents an aromatic or hydrophobic amino acid and/or $X_9$ represents an aromatic or hydrophobic amino acid, or a cysteine (C), an aspartic acid (D), a glutamine (Q), a serine (S), a threonine (T) or a glutamic acid (E); and $X_2$, $X_3$, $X_4$, $X_5$, $X_7$ and $X_8$ each represent a natural or synthetic amino acid, in the presence of various concentrations of test molecule(s);

(ii) separation of the various complexes formed;

(iii) detection of the HLA-DP4/tracer peptide complexes by measuring the signal associated with said tracer peptide; and (iv) selection of the ligand molecules which exhibit a binding activity $IC_{50}$<1000 nM, corresponding to the concentration of these molecules which inhibits 50% of the binding of the tracer peptide.

The residues $X_1$, $X_6$ and $X_9$ of general formula (I) as defined above, which constitute the residues for anchoring in the pockets of the HLA-DP4 molecule, are also called, respectively, residues P1, P6 and P9. Among these residues, the residues X1 (or P1) and X6 (or P6) are the residues which provide the main contribution to the binding to HLA-DP4. The residue $X_9$ or $P_9$ is less important and provides less contribution to the binding to HLA-DP4.

For the purpose of the present invention:

the expression "natural or synthetic amino acids" is intended to mean the 20 natural α-amino acids commonly found in proteins (one-letter code: A, R, N, D, C, Q, E, G, H, I, L, K, M, F, P, S, T, W, Y and V), certain amino acids rarely encountered in proteins (hydroxyproline, hydroxylysine, methyllysine, dimethyl-lysine, etc.), amino acids which do not exist in proteins, such as β-alanine, γ-aminobutyric acid, homocysteine, ornithine, citrulline, canavanine, norleucine, cyclohexylalanine, etc., and the enantiomers and diastereoisomers of the above amino acids;

the term "hydrophobic amino acid" is intended to mean an amino acid selected from (one-letter code): A, V, L, I, P, W, F and M;

the term "aromatic amino acid" is intended to mean an amino acid selected from (one-letter code): F, W and Y.

The use of a tracer peptide, as defined in step (i), makes it possible to effectively select ligands specific for HLA-DP4, i.e. molecules, in particular peptides, which exhibit good affinity for HLA-DP4, i.e. a binding activity<1000 nM.

A tracer peptide in accordance with the invention is selected by carrying out a direct HLA-DP4-binding assay, for example by following steps (i), (ii) and (iii) of the protocol defined above, but in the absence of competitor, corresponding to the test molecule. The appropriate signal detected (fluorescence, etc.) reveals the HLA-DP4/tracer peptide complexes [step (iii)] and the background noise represents the corresponding signal, obtained in the absence of HLA-DP4.

Preferably:

$X_6$ is selected from L, I, W, F, M, Y and C, and $X_1$ is selected from A, V, L, I, W, F, M and Y, and/or $X_9$ is selected from A, V, L, I, P, W, F, M, Y, C, D, Q, S, T and E.

Tracer peptides in accordance with the invention are represented by the peptides NS-p2 (SEQ ID NO:4), MAG 247-258 (SEQ ID NO:9), UL21 283-293 (SEQ ID NO:12), IL3 127-146 (SEQ ID NO:13), UNK1 (SEQ ID NO:14), UL21 283-302 (SEQ ID NO:18) and MAG 245-258 (SEQ ID NO:19).

According to an advantageous embodiment of said method, the tracer peptide is chosen from the group consisting of biotinylated peptides, radiolabeled peptides and peptides coupled to a fluorochrome.

In step (ii), the separation of the formed complexes from the unbound peptides is carried out, for example, by transfer of the formed complexes onto a microtitration plate precoated with an HLA-DP-specific antibody, by chromatography on a gel filtration column or by centrifugation.

When the tracer peptide is radiolabeled or coupled to a fluorochrome, in particular to europium, the HLA-DP4/tracer peptide complexes are detected directly by measuring the radioactivity or the fluorescence emitted by said complexes.

When the tracer peptide is biotinylated, the HLA-DP4/tracer peptide complexes are detected indirectly using conjugated streptavidin, for example by immuno-enzymatic detection using streptavidin conjugated to an enzyme such as alkaline phosphatase, and a substrate for alkaline phosphatase such as 4-methylumbelliferyl phosphate (MUP).

According to another advantageous embodiment of said method, the tracer peptide is used at a concentration <200 nM, preferably less than 20 nM, even more preferably the tracer is used at a concentration of 10 nM.

According to yet another advantageous embodiment of said method, said HLA-DP4 in step (i) is chosen from the group consisting of the molecules encoded by the DPA1*103/DPB1*0401 and DPA1*103/DPB1*0402 alleles.

The method according to the invention advantageously makes it possible to select any HLA-DP4 ligand; this involves both mineral or organic molecules such as peptides and pseudopeptides.

According to another advantageous embodiment of said method, said test molecules represent a library of overlapping peptides covering the sequence of an antigen.

A subject of the present invention is also HLA-DP4 ligands which can be obtained by the method of selection as defined above, corresponding to a mineral or organic, natural or synthetic molecule exhibiting an HLA-DP4-binding activity of less than 1000 nM.

The HLA-DP4-binding activity of a ligand molecule, as defined above, corresponds to the concentration of said ligand molecule which inhibits 50% of the HLA-DP4-binding of a labeled tracer peptide, in a competition assay such as the method of selecting HLA-DP4 ligands defined above.

Among these ligand molecules, mention may in particular be made of peptides and modified peptides such as glycopeptides, lipopeptides, and peptides comprising D-amino acids, pseudopeptide bonds (pseudopeptides) or modifications of the C- or N-terminal ends.

The lipid portion of the ligand lipopeptide is in particular obtained by addition of a lipid unit to an α-amino function of said peptides or to a reactive function of the side chain of an amino acid of the peptide portion; it may comprise one or more chains, derived from $C_4$-$C_{20}$ fatty acids, which are optionally branched or unsaturated (palmitic acid, oleic acid, linoleic acid, linolenic acid, 2-aminohexadecanoic acid, pimelautide, trimexautide) or derived from a steroid. The method of preparing such lipopeptides is in particular described in international applications WO 99/40113 and WO 99/51630. The preferred lipid portion is in particular represented by an $N^\alpha$-acetyl-lysine $N^\epsilon$ (palmitoyl) group, also referred to as Ac—K (Pam).

According to an advantageous embodiment of said HLA-DP4-ligand peptide as defined above, its peptide sequence corresponds to general formula (I) $Z_1X_1X_2X_3X_4X_5X_6X_7X_8X_9Z_2$, in which:

$Z_1$ and $Z_2$, which may be identical or different, are zero or each represent a peptide of 1 to 10 amino acids as defined above, preferably of 1 to 30 amino acids, even more preferably of 1 to 100 amino acids;

$X_6$ represents an aromatic or hydrophobic amino acid, or a cysteine (C);

$X_1$ represents an aromatic or hydrophobic amino acid and/or $X_9$ represents an aromatic or hydrophobic amino acid, or else a cysteine (C), an aspartic acid (D), a glutamine (Q), a serine (S), a threonine (T) or a glutamic acid (E); and $X_2$, $X_3$, $X_4$, $X_5$, $X_7$ and $X_8$ each represent a natural or synthetic amino acid, on condition that said HLA-DP4-ligand peptide of general formula (I) does not correspond to any of the sequences SEQ ID NOS: 1 to 17.

According to an advantageous embodiment of said ligand peptide:

$X_6$ is selected from L, I, W, F, M, Y and C, and $X_1$ is selected from A, V, L, I, W, F, M and Y, and/or $X_9$ is selected from A, V, L, I, P, W, F, M, Y, C, D, Q, S, T and E.

According to an advantageous arrangement of this embodiment, said ligand peptide binds specifically to DPB1*0401 (DPB1*0401-binding activity at least two times greater than the DPB1*0402-binding activity) and $X_6$ is different from C, and/or $X_1$ is different from A and from V, and/or $X_9$ represents W or Y or $X_9$ is different from E and C, and/or $X_4$ is different from K and R.

According to another advantageous arrangement of this embodiment, said ligand peptide binds specifically to DPB1*0402 (DPB1*0402-binding activity at least two times greater than the DPB1*0401-binding activity) and $X_6$ represents C, and/or $X_1$ represents A or V, and/or $X_9$ represents E or C or $X_9$ is different from Y and W, and/or $X_4$ represents K or R.

According to another advantageous embodiment of said ligand peptide, $Z_1$ and $Z_2$ are chosen from the group consisting of:

the sequences of the antigen which are adjacent to the HLA-DP4-restricted CD4+ epitope as defined above, and/or one or more CD8+ T epitopes, and/or multiple CD4+ epitopes, such as peptide 830-846 of the tetanus toxin TT (O'SULLIVAN et al., J. Immunol., 1991, 147, 2663-2669), peptide 307-319 of influenza virus hemagglutinin HA (O'SULLIVAN et al., mentioned above), the Pan DR or PADRE epitope (ALEXANDER et al., DEL GUERCIO et al., FRANKE et al., mentioned above) and peptides derived from the antigens of *Plasmodium falciparum*, such as the CS.T3 peptide (SINIGAGLIA et al., Nature, 1988, 336, 778-780) and the CSP, SSP2, LSA-1 and EXP-1 peptides (DOOLAN et al., J. Immunol., 2000, 165, 1123-1137) and/or one or more B epitopes, for example a peptide or a glycopeptide in which said B epitope consists of a sugar (ALEXANDER et al., mentioned above).

Such sequences advantageously make it possible to trigger or to modulate an immune response in an appropriate manner.

According to yet another advantageous embodiment of said ligand peptide, it has the sequence SEQ ID NO:84 corresponding to the NY-ESO1 87-111 peptide.

The present invention also encompasses the ligand peptides as defined above, which have been polymerized.

A subject of the present invention is also a method of identifying HLA-DP4-ligand peptides as defined above, based on an amino acid sequence, characterized in that it comprises at least the following steps:

a) establishing an HLA-DP4-binding matrix by calculating -for all the mutants of a tracer peptide as defined above, representing all the substitutions of the residues at position 1, 4, 6 or 9 of said tracer peptide with the other 19 natural amino acids- the ratio of the $IC_{50}$ values for said mutant peptides and for said tracer peptide, using the HLA-DP4-binding assay as defined in the method above, b) evaluating the HLA-DP4-binding of peptides of at least 9 amino acids included in said amino acid sequence, by calculating, for each fragment of 9 amino acids of said peptide, the sum of the scores for HLA-DP4-binding of the residues at positions 1, 4, 6 and 9 of said fragment, using the binding matrix established in a), and c) identifying the HLA-DP4-ligand peptides corresponding to those to which the loss of HLA-DP4-binding, relative to said tracer peptide, is smallest, i.e. those for which the sum of the binding scores has the lowest value expressed as a logarithm (log); preferably less than 2, preferably less than 1, even more preferably close to 0.

This HLA-DP4-binding matrix which is illustrated for the reference peptide UNK 3-15 (SEQ ID NO:28), in table XIV of example 6, makes it possible to estimate the HLA-DP4-binding activity of any peptide of at least 9 amino acids; peptides having binding scores of, respectively, 0, 1, 2, 3 and 4 correspond to peptides exhibiting a 1-fold, 10-fold, 100-fold, 1000-fold and 10 000-fold loss of binding relative to the UNK 3-15 peptide (IC$_{50}$ 10 nM), i.e. exhibiting an estimated binding activity of, respectively, 10 nM, 100 nM, 1000 nM, 10 µM and 100 µM.

For example, the tumor antigen NY-ESO1 comprises a peptide WITQCFLPV (SEQ ID NO: 132) having a DP*0401- and DP*0402-binding score of 0+0.3+0+0.3=0.6 corresponding to an estimated binding activity (using the HLA-DP4-binding matrix) of 39 nM and a calculated activity (using the DP*0401- and DP*0402-binding assay) of, respectively, 20 nM and 67 nM.

The method of identifying HLA-DP4-ligand peptides according to the invention, which is easy to implement and can be automated, makes it possible, in particular using appropriate software, to predict the sequence of the HLA-DP4-ligand peptides present in all proteins representing antigens of interest. The peptide sequences thus identified can then be verified using an HLA-DP4-binding assay, defined in the method of selecting HLA-DP4 ligands according to the invention.

A subject of the present invention is also a nucleic acid molecule, characterized in that it encodes a ligand peptide as defined above.

The subject of the invention also encompasses the recombinant nucleic acid molecules comprising at least one nucleic acid molecule in accordance with the invention, linked to at least one heterologous sequence.

For the purpose of the present invention, the expression "sequence which is heterologous relative to a nucleic acid sequence encoding a ligand peptide" is intended to mean any nucleic acid sequence other than those which, naturally, are immediately adjacent to said nucleic acid sequence encoding a peptide.

The subject of the present invention encompasses in particular:
- expression cassettes comprising at least one nucleic acid molecule in accordance with the invention and the sequences required for controlling the transcription and the translation of said nucleic acid molecule (promoter, intron, initiation codon (ATG), stop codon, polyadenylation signal), and
- recombinant vectors comprising an insert consisting of a nucleic acid molecule in accordance with the invention. Advantageously, these expression vectors comprise at least one expression cassette as defined above.

Many vectors into which a nucleic acid molecule of interest can be inserted in order to introduce it into and to maintain it in a eukaryotic or prokaryotic host cell are known in themselves; the choice of a suitable vector depends on the use envisioned for this vector (for example, replication of the sequence of interest, expression of this sequence, maintenance of this sequence in extrachromosomal form, or else integration into the host's chromosomal material), and also on the nature of the host cell.

For example, use may be made, inter alia, of viral vectors such as adenoviruses, retroviruses, lentiviruses and AAVs, into which the sequence of interest has been inserted beforehand; said sequence (isolated or inserted into a plasmid vector) can also be combined with a substance which allows it to cross the host cell membrane, for example a preparation of liposomes, of lipids or of cationic polymers, or it can be injected directly into the host cell, in the form of naked DNA.

A subject of the invention is also prokaryotic or eukaryotic cells transformed with at least one nucleic acid molecule in accordance with the invention.

Transformed cells in accordance with the invention can be obtained by any means, known in themselves, making it possible to introduce a nucleic acid molecule into a host cell. For example, in the case of animal cells, use may be made of the vectors or the lipid preparations as defined above.

A subject of the present invention is also an immunomodulatory composition, characterized in that it comprises at least one HLA-DP4 ligand or a nucleic acid molecule encoding an HLA-DP4-ligand peptide as defined above, and a pharmaceutically acceptable vehicle.

Advantageously, said nucleic acid molecule is included in a vector as defined above.

Depending on the choice of the HLA-DP4 ligand and of its mode of presentation (route of administration, dose, possible addition of adjuvant) such an immunomodulatory composition results in either activation of T lymphocytes, or the anergy thereof.

In fact, it has been shown that a single subcutaneous injection of a small amount of peptide results in anergy (OLD-FIELD et al., *J. Immunol.*, 2001, 167, 1734-1739). On the other hand, it is known that repeated injections of large amounts of peptide in the presence of adjuvant result in T lymphocyte activation. In addition, culmination with $Z_1$ and $Z_2$ peptides as defined above also makes it possible to increase the antigen-specific immune response (ALEXANDER et al., mentioned above).

Consequently, said composition is used both for immunization against a pathogenic agent or a tumor cell and for the treatment of autoimmune diseases (multiple sclerosis, insulin-dependent diabetes), of allergy or of transplant rejection.

A subject of the present invention is also a reagent for diagnosing the immune state of an individual, characterized in that it comprises at least one HLA-DP4 ligand as defined above, optionally labeled or complexed, in particular complexed with labeled (biotinylated) HLA-DP4 molecules, in the form of multimeric complexes such as tetramers.

A subject of the present invention is also the use of an HLA-DP4 ligand or of a nucleic acid molecule encoding an HLA-DP4-ligand peptide as defined above, for preparing an immunomodulatory medicinal product or a reagent for diagnosing the immune state of an individual.

For the purpose of the present invention, the expression "diagnosing the immune state of an individual" is intended to mean detecting the presence, in said individual, of CD4+ T lymphocytes specific for an antigen derived from a pathogenic agent or from a tumor cell, for an allergen, for an alloantigen or for an autoantigen.

The reagent in accordance with the invention which is capable of detecting the presence of CD4+ T lymphocytes specific for an antigen is used for detecting: an infection with a pathogenic agent, a cancer, an autoimmune disease, an allergy or a transplant rejection, based on a biological sample from a patient.

A subject of the present invention is also a method of diagnosing the immune state of an individual, comprising the steps of:
- bringing a biological sample from said individual into contact with a diagnostic reagent as defined above, and
- detecting the CD4+ T lymphocytes specific for an antigen by any suitable means.

A subject of the present invention is also a kit for detecting the immune state of an individual, characterized in that it comprises at least one reagent as defined above, combined with a means for detecting CD4+ T lymphocytes specific for an antigen.

The CD4+ T lymphocytes specific for an antigen are detected by any means known in themselves. For example, use may be made of direct means such as lymphocyte proliferation assays or flow cytometry in the presence of multimeric complexes as defined above, or else indirect means, for instance the assaying of cytokines such as IL2, IL4, IL5 or γIFN, in particular by immunoenzymatic techniques (ELISA, RIA, ELISPOT).

More precisely:

*as regards the proliferation assay:

A suspension of cells (PBMCs, CD8+ cell-depleted PBMCs, T lymphocytes pre-enriched by a step consisting in culturing in vitro with the peptides as defined above, or cloned T lymphocytes) is cultured for 3 to 5 days in the presence of said HLA-DP4 ligands and, as needed, of appropriate pre-senting cells, such as dendritic cells, autologous or heterologous PBMCs, lymphoblastoid cells such as those obtained after infection with the EBV virus or genetically modified cells. The proliferation of the cells is measured by incorporation of tritiated thymidine into the DNA of the cells. The peptides as defined above make it possible to detect in the initial suspension the presence of cells specific for these peptides.

*as regards the ELISPOT assay:

The ELISPOT assay makes it possible to detect the presence of γIFN-secreting T cells specific for a peptide as defined above.

More precisely, the T cells are detected by measuring the secretion of γIFN after incubation of the PBMCs from patients with said peptides in accordance with the method described in International Application WO 99/51630 or Gahéry-Ségard et al., (J. Virol., 2000, 74, 1964).

*as regards the use of multimeric complexes and in particular of tetrameric complexes:

a biological sample, preferably peripheral blood mononuclear cells (PBMCs), is brought into contact with tetrameric complexes as defined above, and labeled cells are analyzed by flow cytometry.

Advantageously, prior to bringing the biological sample into contact with said complex, it is enriched in CD4+ T cells by bringing it into contact with anti-CD4 antibodies so as to enrich said sample.

The tetramers are prepared as specified, for example, in NOVAK et al. (J. Clin. Investig., 1999, 104, R63-R67) or in KURODA et al. (J. Virol., 2000, 74, 18, 8751-8756).

Briefly, the tetramers are produced by incubating, for 72 hours at 37° C. and in a 10 mM citrate phosphate buffer containing 0.15 M NaCl, at a pH of between 4.5 and 7, soluble and biotinylated HLA II molecules with a 10-fold excess of HLA-DP4 ligands as defined above.

The tetramerized form is obtained by adding streptavidin labeled with a fluorochrome to the preparation, in an amount four times less (mole for mole) than the amount of HLA II molecules. The entire mixture is incubated overnight at ambient temperature.

To use these tetramers, a suspension of cells (PBMCs, CD8+ cell-depleted PBMCs, T lymphocytes pre-enriched by a step consisting in culturing in vitro with the HLA-DP4 ligands as defined above, or cloned T lymphocytes) is brought into contact with one or more tetramers (10 to 20 mg/ml) for 1 to 3 hours. After washing, the suspension is analyzed by flow cytometry: the labeling of the cells with the tetramers is visualized by virtue of the fact that these constructs are fluorescent.

The flow cytometry makes it possible to separate the cells labeled with the tetramers from the nonlabeled cells and to thus perform cell sorting.

A subject of the present invention is thus also a method of sorting CD4+ T lymphocytes specific for an antigen, characterized in that it comprises at least the following steps:

bringing a cell sample into contact with tetramers labeled with a fluorochrome, prepared from complexes between HLA-DP4 ligands as defined above and soluble HLA-DP4 molecules, and sorting these cells bound to said tetramers, by flow cytometry.

Figure 2:
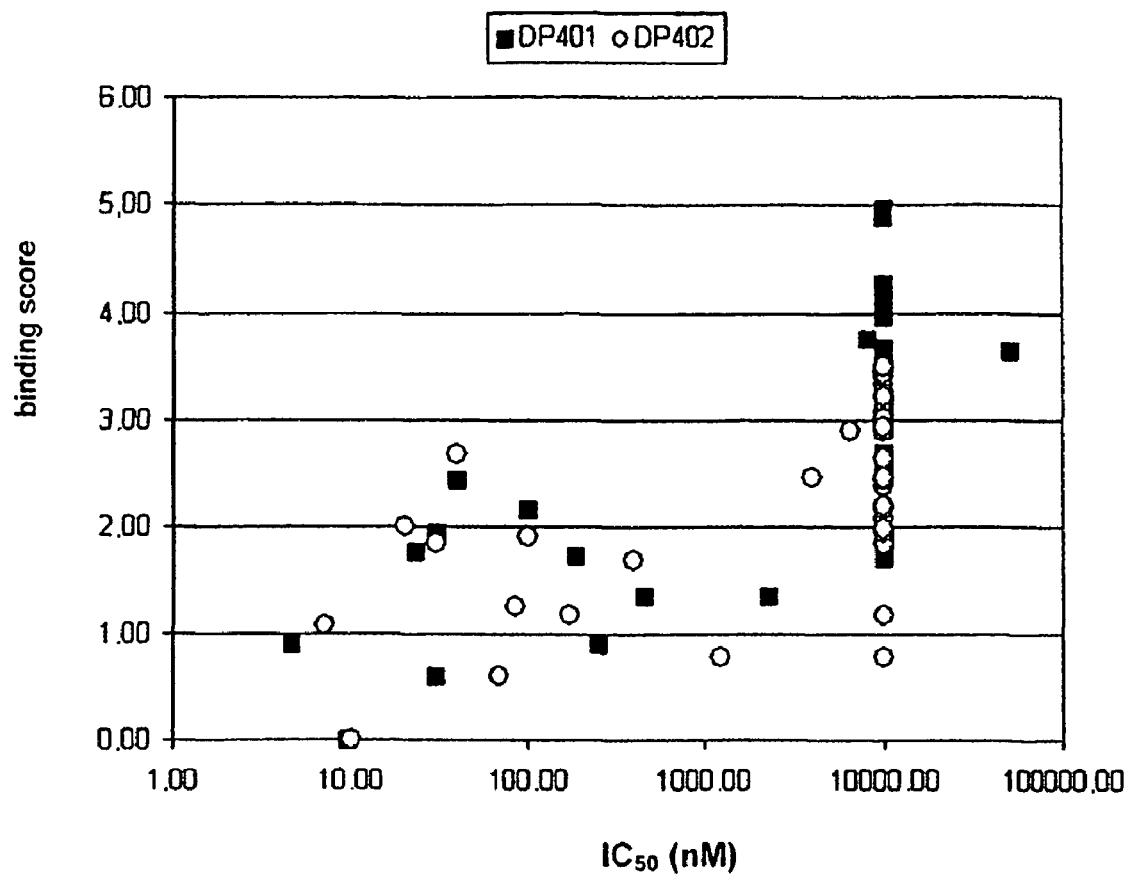

Besides the above arrangements, the invention also comprises other arrangements, which will emerge from the following description which refers to examples of implementation of the subject of the present invention, with references to the attached drawings in which:

FIG. 1 illustrates the activity of binding of peptides to the HLA-DP4 molecules encoded, respectively, by DPB1*0401 (A) and DPB1*0402 (B), determined according to the method in accordance with the invention with, as tracer peptide, the biotinylated UNK1 peptide (10 nM); the percentage of DP4 molecule-binding is expressed as a function of the molar concentration of the peptides. The maximum binding (100%) corresponds to the value obtained for the tracer peptide alone, in the absence of competitor peptide. UNK: UNK1 (SEQ ID NO:14), IL: IL3 127-146 (SEQ ID NO:13), MAG: MAG 245-258 (SEQ ID NO:19), NSP2: SEQ ID NO:4, TT: TT 947-963 (SEQ ID NO:20), DQB: DQB 43-57 (SEQ ID NO:23), HCI 46-63: SEQ ID NO:24) and HA: HA 306-318 (SEQ ID NO:21), FIG. 2 illustrates the correlation between the HLA-DP4-binding score (estimated by the method of identifying HLA-DP4-ligand peptides in accordance with the invention) and the affinity for the HLA-DP4 molecules (determined by the $IC_{50}$ value, measured using the HLA-DP4-binding assay defined in the method of selecting HLA-DP4-ligand peptides in accordance with the invention) analyzed on a set of 44 peptides.

EXAMPLE 1

Principle of the HLA-DP4/Peptide Binding Assay

1) Peptide Preparation

All the peptides were synthesized according to the Fmoc strategy in parallel solid-phase synthesis, purified by HPLC and controlled by mass spectrometry (ES-MS).

The peptides are biotinylated on their $NH_2$-terminal residue, according to the protocol as described in Texier et al., mentioned above.

2) Antibody Preparation

The HLA-DP molecule-specific antibodies, such as the antibody B7/21 (WATSON, et al., Nature, 1983, 304, 358-361), are purified from the culture supernatant of the corresponding hybridomas, on protein A-sepharose columns. These antibodies are then coupled onto sepharose 4B or protein A-sepharose columns for purification of the HLA-DP4 molecules.

More precisely, after centrifugation at 1100 g, the culture supernatant of the B7/21 antibody-producing cells is filtered through 0.22 μm and its pH is adjusted to 7-8 with 0.1 M Tris-HCl buffer, pH 8. This supernatant is then applied to a 10 ml protein A-sepharose 4 fast flow column prewashed with 100 ml of 0.1 M Tris-HCl buffer, pH 8. The column is then washed with 100 ml of 0.1 M Tris-HCl buffer, pH 8, and 100 ml of 0.01 M Tris-HCl buffer, pH 8. The antibodies are eluted with 0.1 M glycine-HCl buffer, pH 3. The column is rinsed with 100 ml of 0.1 M Tris-HCl buffer, pH 8. The eluted fraction which contains the B7/21 antibody is immediately neutralized with 1 M Tris-HCl buffer, pH 8, before being thoroughly dialyzed against 0.1 M borate buffer, pH 8.2. The amount of antibodies obtained is determined based on the optical density (OD) at 278 nm.

The affinity columns intended for purification of the HLA-DP4 molecules are prepared in the following way: 0.75 g of protein A-sepharose 4B (3 ml of final gel) is swollen in water and then in 0.1 M borate buffer pH 8.2. 15 mg of monoclonal antibody, such as B7/21, in 0.1 M borate buffer, pH 8.2, are added to the gel, centrifuged beforehand. The coupling is carried out for two hours at ambient temperature and then controlled by absorbence of the supernatant at 278 nm. The gel is then washed successively with 100 ml of 0.1 M borate buffer, pH 8.2, 120 ml of 0.2 M triethanolamine buffer, pH 8.2, 120 ml of 20 mM dimethylpyrimidate buffer, 0.2 M triethanolamine, pH 8.2 and 150 ml of 0.2 M ethanolamine buffer, pH 8.2. After the gel has been poured, it is rinsed with 150 ml of 0.1 M borate buffer, pH 8.2. The final control for the coupling is performed by an elution in 0.1 M glycine buffer, pH 2.5, containing 0.5 M NaCl; the absorbence at 278 nm of the 1 ml fractions should be less than 0.1. The column is immediately rinsed with 50 ml of 0.1 M borate buffer, pH 8.2, and 20 ml of 0.1 M borate buffer containing 0.02% NaN$_3$, pH 8.2. It is stored in this buffer at 4° C. until use.

3) Purification of the HLA-DP4 Molecules

The HLA-DP4 molecules are purified from various human B lymphocyte lines transformed with the Epstein Barr virus (EBV), which are homozygotes for DP, by immunoaffinity using monoclonal antibodies specific for all DP molecules. The origin of the lines and the alleles which characterize them are indicated in table IV.

TABLE IV

| Lines | DP specificity | DPA1 allele | DPB1 allele | Reference |
|---|---|---|---|---|
| HOM2 | DP4 | DPA1*0103 | DPB1*0401 | ♣ |
| BOLETH | DP4 | DPA1*0103 | DPB1*0401 | ♣ |
| PITOUT | DP4 | DPA1*0103 | DPB1*0401 | SOUTHWOOD et al., mentioned above |
| HHKB | DP4 | DPA1*0103 | DPB1*0401 | DAVENPORTH et al., P.N.A.S., 1995, 92, 6567 |
| SHU | DP4 | DPA1*0103 | DPB1*0402 | ♣ |
| MLF | DP4 | DPA1*0103 | DPB1*0402 | ♣ |
| BM92 | DP4 | DPA1*0103 | DPB1*0402 | ♣ |

♣the origin of the lines is described on the internet site of the European cell culture collection (http://fuseiv.co.uk/camr/).

The HLA-DP4 molecules are purified from a pellet of these EBV-transformed human cells, according to a protocol derived from those used for the HLA-DR molecules (GORGA et al., *J. Biol. Chem.*, 1987, 262, 16087; TEXIER et al., mentioned above).

More precisely, 5 to 6×10$^9$ cells are lysed at a concentration of approximately 10$^8$ cells/ml in lysis buffer (0.01 M Tris, 0.15 M NaCl, 0.02% NaN$_3$, pH 7, 1% NP40, 10 µg/ml aprotinin, 5 mM EDTA, 10 µM PMSF) in ice for 30 minutes. The large cell debris is removed from the lysis medium by centrifugation at 1100 g for 10 minutes at 4° C. The supernatant is then ultracentrifuged at 100 000 g at 4° C. for 1 hour. The rest of the purification takes place in a cold room at 4° C. The lysate is passed successively over a sepharose 4B column (10 ml of gel prepared in 1×PBS), a protein A-sepharose 4B column (5 ml of gel prepared in 1×$^2$PBS) and then over the anti-DP affinity column. The columns are then rinsed with 250 ml of lysis buffer. The sepharose 4B column is discarded. The protein A-sepharose 4B column is rinsed with 25 ml of 1×TBS buffer (0.01 M Tris, 0.15 M NaCl, 0.02% NaN$_3$, pH 7), 50 ml of (0.1 M glycine; 0.5 M NaCl, pH 2.5) buffer and 200 ml of 1×PBS buffer, before being stored at 4° C. The anti-DP column is rinsed with 250 ml of TBS buffer containing 1 mM of dodecyl maltoside (DM). It is then eluted individually with the elution buffer (100 mM Na$_2$CO$_3$, 500 mM NaCl, 0.02% NaN$_3$, 1.1 mM DM, pH 11.5) in 15 fractions of 3 ml. The eluate is immediately neutralized with 10% of buffer (2 M Tris-HCl, pH 6.8), and then thoroughly dialyzed at 4° C. against 1×PBS buffer containing 1 mM of DM.

4) HLA-DP4-Peptide Binding Assay

The assay for binding of the peptides to the HLA-DP4 molecules is a competition assay with immunoenzymatic detection, derived from that developed for HLA-DR molecules (HLA-DR1: MARSHALL et al., mentioned above), HLA-DR1, -DR2, -DR3, -DR4, -DR7, -DR11 and -DR13: patent FR 99 0879 and TEXIER et al., mentioned above). It is carried out in 96-well plates, which makes it possible to study many samples in the same experiment. Briefly, the purified HLA-DP4 molecules are incubated with a biotinylated peptide which serves as a tracer, and various concentrations of the test peptide. The biotinylated peptide is a DP4-ligand peptide; it is a peptide recognized by DP4-specific CD4+ T lymphocytes, such as those specified in table III above, or a new peptide isolated using the present DP4-binding assay. Among these peptides, mention may be made, for example, of the UNK1 peptide or the IL3 127-146 peptide. The incubation is carried out in a buffer, the pH of which can vary. It is generally 5, and the incubation generally lasts 24 h. After incubation, the samples are neutralized, and then 100 µl of each sample is transferred onto an ELISA plate pre-coated with an anti-DP antibody, such as B7/21. The HLA-DP molecule/biotinylated peptide complexes attached to the bottom of the plate via the antibody are revealed by means of streptavidin phosphatase and a fluorescent substrate. The activity of each peptide is characterized by the concentration which inhibits 50% of the binding of the biotinylated peptide (IC$_{50}$).

EXAMPLE 2

Determination of the Binding Assay Parameters

1) Tracer Peptide a) Materials and Methods

The binding of peptides to the two DP4 molecules (DP401 encoded by the DPA1*0103/DPB1*0401 allele and DP402 encoded by the DPA1*0103/DPB1*0402 allele) was analyzed by ELISA using the following direct binding assay:

The HLA-DP4 molecules purified according to the protocol described in example 1 are diluted 10 times in 10 mM phosphate buffer (1/10 dilution). They are then incubated with various concentrations of a biotinylated peptide (10$^{-6}$ M, 10$^{-7}$ M and 10$^{-8}$ M) in 10 mM phosphate buffer containing 150 mM NaCl, 1 mM DM, 10 mM citrate and 0.003% thimerosal, pH 5, in 96-well polypropylene plates, for 24 h at 37° C. Samples without DP4 molecules are used as a control. At the end of the incubation, the samples are neutralized with 50 µl of 450 mM Tris-HCl buffer, pH 7.5, containing 0.003% thimerosal, 0.3% BSA and 1 mM DM. They are then transferred onto 96-well maxisorp ELISA plates onto which the anti-DP antibodies have been pre-adsorbed. Specifically, 10 µg/ml of anti-DP antibodies were incubated overnight at 4° C. (100 µl/well) and the plates were then saturated with the 100 mM Tris-HCl buffer, pH 7.5, containing 0.3% BSA and 0.003% thimerosal overnight at 4° C. The incubation of the samples on these plates is carried out for two hours at ambient temperature, like the remainder of the assay, and then extensive washing is performed, between each step, in 0.1 M Tris-HCl buffer, pH 7.5, containing 0.05% Tween-20. The biotinylated peptide bound to the HLA-DP molecules is detected by adding 100 μl/well of the streptavidin-alkaline phosphatase conjugate (45 minutes) diluted 1/2000 in the 10 mM Tris buffer, pH 7, containing 0.15 M NaCl, 0.05% Tween 20, 0.2% BSA and 0.003% thimerosal, and then by adding 200 μl/well of 100 μM MUP substrate in 0.05 M NaHCO$_3$ buffer, pH 9.8, containing 1 mM MgCl$_2$. The emission of fluorescence by the product of the enzymatic reaction is measured at 450 nm after excitation at 365 nm, and the ratio of the values obtained with or without DP4 is determined ($R_F$=fluorescence value in the presence of DP4/fluorescence value in the absence of DP4).

b) Results

The DP401 molecule-binding of peptides derived from the DP4-ligand peptides described above (table III) was assayed:

peptide bUL21 283-302 (RELWWVFYAGDRALEEPHAE; SEQ ID NO: 18)

peptide bIL3 127-146 (SEQ ID NO:13)

peptide bMAG 245-258 (LLTQHFVQENYLEY; SEQ ID NO:19)

peptide bMT 451-466 (SEQ ID NO:6)

peptide bNS-p2 (SEQ ID NO:4)

peptide bTT 947-963 (FNNFTVSFWLRVPKVSA; SEQ ID NO:20)

peptide bUNK1 (SEQ ID NO:14)

Two peptides specific, respectively, for DR1 and for DR7 were used as control for the DP4-binding specificity:

peptide bHA 306-318 (PKYVKQNTLKLAT; SEQ ID NO:21) described by HILL et al., *J. Immunol.*, 1994, 152, 2890, and peptide bYKL (AAYAAAKAAALAA; SEQ ID NO:22) described by MARSHALL et al., mentioned above.

The results are given in table V.

TABLE V

Selection of the tracers using a direct HLA-DP4-binding assay

| | $R_F$ = fluorescence value in the presence of DP4/ fluorescence value in the absence of DP4 | | |
|---|---|---|---|
| peptide | $10^{-6}$ M | $10^{-7}$ M | $10^{-8}$ M |
| bUL21 283-302 | 8.3 | 13.3 | 10.1 |
| bIL3 127-146 | 10 | 20 | 17.3 |
| bMAG 245-258 | 1.5 | 6.7 | 5.4 |
| bMT 451-466 | 5.5 | 4 | 2 |
| bNS-p2 | 1 | 4.2 | 7.8 |
| bTT 947-963 | 1.7 | 3.6 | 2.7 |
| bUNK1 | 21.6 | 21.7 | 20 |
| bHA 306-318 | 4.9 | 4.7 | 2.7 |
| bYKL | 4.8 | 3.2 | 3 |

The results show that:

the bUNK1 and bIL3 127-146 peptides have a high DP4-binding capacity, the bTT 947-963 and bMT 451-466 peptides have a low binding capacity, and the bNS-p2, pUL21 283-302 and bMAG 245-258 peptides have an intermediate binding capacity.

The peptides exhibiting an $R_F>5$ at the concentration of $10^{-8}$ M are considered to be good tracers which can be used in the binding assay.

The UNK1 peptide, which gave the best results, was used to optimize the binding assay.

2) Time, pH, Concentration of the Tracer Peptide

In order to have a sensitive and DP4-specific assay, the concentration of HLA-DP4 molecules, the concentration of the biotinylated peptide, the pH and the peptide/HLA-DP4 molecule incubation time were optimized with the bUNK1 peptide.

a) Materials and Methods

The HLA-DP4 molecules purified according to the protocol described in example 1 were diluted 1/10, 1/20, 1/40 and 1/80 in 10 mM phosphate buffer containing 150 mM of NaCl, 1 mM DM, 10 mM citrate and 0.003% thimerosal, at various pH values (pH 4, 5, 5.5, 6, 6.5 and 7), with the bUNK1 peptide at various concentrations and several concentrations of competitor peptides, in 96-well polypropylene plates. At the end of the incubation at 37° C., the samples were neutralized with 50 μl of 450 mM Tris-HCl buffer, pH 7.5, containing 0.003% thimerosal, 0.3% BSA and 1 mM DM. They were then transferred onto 96-well maxisorp ELISA plates onto which the anti-DP antibodies had been pre-adsorbed. Very specifically, 10 μg/ml of anti-DP antibodies were incubated overnight at 4° C. (100 μl/well) and the plates were then saturated with the 100 mM Tris-HCl buffer, pH 7.5, containing 0.3% BSA and 0.003% thimerosal overnight at 4° C. The incubation of the samples on these plates was carried out for two hours at ambient temperature, like the remainder of the assay, and then thorough washing was performed, between each step, in 0.1 M Tris-HCl buffer, pH 7.5, containing 0.05% Tween-20. The biotinylated peptide bound to the HLA-DP molecules was detected by adding 100 μg/well of the streptavidin-alkaline phosphatase conjugate (45 minutes) diluted 1/2000 in the 10 mM Tris buffer, pH 7, containing 0.15 M NaCl, 0.05% Tween 20, 0.2% BSA and 0.003% thimerosal, and then by adding 200 μl/well of 100 μM MUP substrate in 0.05 M NaHCO$_3$ buffer, pH 9.8, containing 1 mM MgCl$_2$. The emission of fluorescence by the product of the enzymatic reaction was measured at 450 nm after excitation at 365 nm. The maximum binding was determined by incubating the biotinylated peptide with the MHC II molecule in the absence of competitor peptide. The binding specificity was controlled by adding an excess of nonbiotinylated peptide. The background noise obtained does not differ significantly from that obtained by incubating the biotinylated peptide in the absence of the MHC II molecules.

The results are expressed in the form of the concentration of competitor peptide which inhibits 50% of the maximum binding of the labeled peptide ($IC_{50}$).

b) Results

The optimum conditions are given in table VI:

TABLE VI

Conditions for the DP4 molecule-binding assay

| Molecules | DPA1*0103/ DPB1*0401 | DPA1*0103/ DPB1*0402 |
|---|---|---|
| Biotinylated peptide | bUNK 1-17 | bUNK 1-17 |
| Concentration | 10 nM | 10 nM |
| pH | 5 | 5 |
| Incubation time | 24 h | 24 h |

TABLE VI-continued

Conditions for the DP4 molecule-binding assay

| Molecules | DPA1*0103/<br>DPB1*0401 | DPA1*0103/<br>DPB1*0402 |
|---|---|---|
| Concentration<br>of HLA-DP4 | | Dilution 1/20 to<br>1/40 ♣ |

♣the dilutions indicated are carried out using the preparation of purified HLA-DP4 molecules obtained in example 1.

EXAMPLE 3

Sensitivity and Specificity of the DP4 Molecule-Binding Assay a) Specificity

The results illustrated in FIG. 1 show that the binding activity measured in the assay is specific for HLA-DP4 insofar as:
 peptides known to be ligands for DP4 molecules effectively bind the HLA-DP*0401 and 0402 molecules. They are the IL3 127-146 peptide (naturally present on a DP4 molecule), DP4-restricted CD4+ T lymphocyte-specific peptides: NS-p2 (or NSP2), TT 947-963 and, to a lesser extent, the MAG 245-258 peptide, and
 peptides known to bind other HLA II molecules do not bind to the HLA-DP*0401 and 0402 molecules. They are the peptides: DQB 43-57 (DVEVYRAVTPLGPPD, SEQ ID NO:23), HCI 46-63 (EPRAPWIEQEGPEYWDQE, SEQ ID NO:24) and HA 306-318 (SEQ ID NO:21) which are known to bind, respectively, to HLA-DQ3, HLA-DQ2 and HLA-DR molecules (MARSHALL et al., mentioned above, JOHANSEN et al., *Immunogenetics*, 1996, 45, 142).

The specificity of the assay results from the use:
 of an HLA-DP molecule-specific antibody for the purification and for the adsorption of the ELISA plates, and
 of the biotinylated peptide which binds with high affinity; FIG. 1 shows that the UNK peptide, which is the nonbiotinylated counterpart of the bUNK tracer peptide, completely inhibits the binding of the tracer both to the HLA-DPB1*0401 molecule and to the DPB1*0402 molecule.

b) Sensitivity

The sensitivity of the assay is reflected by the $IC_{50}$ observed with the nonbiotinylated peptide (UNK1) corresponding to the tracer (bUNK1). FIG. 1 indicates that the values of, respectively, 8 and 9 nM for DPB1*0401 and DPB1*0402 reflect good sensitivity.

FIG. 1 also shows that the DPB1*401 molecule-binding and DPB1*402 molecule-binding activities of the peptides, although comparable, are different. These results confirm that the DPB1*401 and DPB1*402 molecules exhibit differences which can be detected by this binding assay.

EXAMPLE 4

Screening for HLA-DP4-Ligand Peptides Using a Peptide Library

1) Materials and Methods

The overlapping peptides carrying the complete sequence of the major allergen of bee venom (Api m1), described in patent FR 99 00879, were synthesized and subjected to the DP401 molecule-binding and DP402 molecule-binding assays, under the conditions defined in table VI.

2) Results

The results are given in table VII below:

TABLE VII

Binding of the Api m1 peptides to the HLA-DPB1*0401 and DPB1*0402 molecules

| | $IC_{50}$ (nM) | |
|---|---|---|
| Peptide | DP0401 | DP0402 |
| 1-18 | >10 000 | >10 000 |
| 5-22 | >10 000 | >10 000 |
| 9-26 | >10 000 | >10 000 |
| 13-30 | >10 000 | >10 000 |
| 17-34 | >10 000 | >10 000 |
| 21-38 | >10 000 | >10 000 |
| 25-42 | >10 000 | >10 000 |
| 29-46 | >10 000 | >10 000 |
| 33-50 | >10 000 | >10 000 |
| 37-54 | >10 000 | >10 000 |
| 41-58 | >10 000 | >10 000 |
| 45-62 | >10 000 | >10 000 |
| 49-66 | >10 000 | >10 000 |
| 53-70 | >10 000 | >10 000 |
| 57-74 | >10 000 | >10 000 |
| 61-78 | >10 000 | >10 000 |
| 65-82 | 50 000 | 6500 |
| 69-86 | >10 000 | >10 000 |
| 73-90 | >10 000 | >10 000 |
| 77-94 | 450 | 175 |
| 81-98 | 2250 | 1225 |
| 85-102 | >10 000 | >10 000 |
| 89-106 | >10 000 | >10 000 |
| 93-110 | >10 000 | >10 000 |
| 97-114 | >10 000 | >10 000 |
| 101-118 | >10 000 | >10 000 |
| 105-122 | >10 000 | >10 000 |
| 109-126 | >10 000 | >10 000 |
| 113-130 | >10 000 | >10 000 |
| 117-134 | >10 000 | >10 000 |

These results show that peptide 77-94 of the major antigen of bee venom 94 (Api m1 77-94: TISSYFVGKMYFN-LIDTK, SEQ ID NO:17) is a peptide which is a ligand for the DPB1*0401 and DPB1*0402 molecules.

EXAMPLE 5

Determination of the DP4 Molecule-Binding Units

1) Materials and Methods a) Determination of a Minimum Peptide Derived from UNK1 Capable of Binding to the DP4 Molecules Peptides derived from the UNK1 peptide (UNK 1-17, SEQ ID NO:14) comprising increasing deletions at one of the $NH_2$ or COOH ends, or at both ends, were synthesized. The sequence of these peptides (UNK 1-11, 1-12, 1-13, 2-14, 3-15, 4-16, 5-17, 6-17, 7-17, 3-17 and 1-15) corresponding, respectively, to SEQ ID NOS:25-26, 16 and 27-34 is given in table VIII. The binding activity of the peptides, expressed by the $IC_{50}$ value, was determined using the competition binding assay, under the conditions defined in table VI.

b) Determination of the Tesidues of the UNK1 Peptide which are Involved in Binding to the DP4 Molecules Mutants of the UNK 3-15 peptide (KYFAATQFEPLAA; SEQ ID NO:28) were synthesized; each mutant contains only one of the residues Y4, F5, T8, Q9, F10, E11, P12 and L13 substituted with alanine or with lysine, the residue K3 substituted with alanine, or else one of the residues A6, A7, A14 and A15 substituted with lysine.

The sequence of these peptides (UNK K3A, Y4A, F5A, T8A, Q9A, F10A, E11A, P12A, L13A, Y4K, F5K, A6K, A7K, T8K, Q9K, F10K, E11K, P12K, L13K, A14K and A15K) corresponding, respectively, to the sequences SEQ ID NOS:35 to 55 is given in table IX.

The binding activity of the peptides, expressed by the $IC_{50}$ value, was determined using the competition binding assay, under the conditions defined in table VI. The loss of binding of the mutant peptides is expressed by the ratio of the $IC_{50}$ values for the mutant peptide and for the UNK1 peptide.

c) Determination of the DP401 Molecule-Binding and DP402 Molecule-Binding Units

The residues F in P1, T in P4, F in P6 or L in P9 of the UNK1 peptide were substituted with one of the following residues:

P1: Y,L,E,N,T,D,G,H,I,M,P,Q,R,S,V or W,
P4: F,L,E,D,N,Y,R,S,G,H or P
P6: Y,L,W,E,N,T,D,G,H,I,M,P,Q,R,S,V,W or C,
P9: F,Y,E,D,N,R,V,G,H,I,P,Q,S,T or W.

The sequence of these peptides, corresponding to the sequences SEQ ID NOS: 56 to 81 and SEQ ID NOS:96 to 129, is given, respectively, in tables Xa and Xb.

The loss of DP4 molecule-binding of the mutant peptides was determined using the assay described for the alanine and lysine mutants.

2) Results a) Determination of a Minimum UNK1 Peptide

The results are given in table VIII below:

TABLE VIII

Binding to DP401 and DP402 of the peptides derived from UNK1 (UNK 1-17)
(SEQ ID NOS: 14, 25, 26, 16 and 27-34, respectively, in order of appearance)

| Peptides | Position of the sequences | | | | | | | | | | | | | | | | | $IC_{50}$ (nM) | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 401 | 402 |
| UNK1-17 | E | K | K | Y | F | A | A | T | Q | F | E | P | L | A | A | R | L | 11 | 14 |
| UNK1-11 | E | K | K | Y | F | A | A | T | Q | F | E | | | | | | | 55 | 95 |
| UNK1-12 | E | K | K | Y | F | A | A | T | Q | F | E | P | | | | | | 93 | 100 |
| UNK1-13 | E | K | K | Y | F | A | A | T | Q | F | E | P | L | | | | | 14 | 28 |
| UNK2-14 | | K | K | Y | F | A | A | T | Q | F | E | P | L | A | | | | 15 | 23 |
| UNK3-15 | | | K | Y | F | A | A | T | Q | F | E | P | L | A | A | | | 19 | 23 |
| UNK4-16 | | | | Y | F | A | A | T | Q | F | E | P | L | A | A | R | | 38 | 25 |
| UNK5-17 | | | | | F | A | A | T | Q | F | E | P | L | A | A | R | L | 65 | 38 |
| UNK6-17 | | | | | | A | A | T | Q | F | E | P | L | A | A | R | L | 15000 | 6000 |
| UNK7-17 | | | | | | | A | T | Q | F | E | P | L | A | A | R | L | 15000 | 12500 |
| UNK3-17 | | | K | Y | F | A | A | T | Q | F | E | P | L | A | A | R | L | 18 | 14 |
| UNK1-15 | E | K | K | Y | F | A | A | T | Q | F | E | P | L | A | A | | | 18 | 17 |

The results obtained show that:
- the loss of binding observed with the UNK 1-11, UNK 1-12, UNK 4-16 and UNK 5-17 peptides suggests that the minimum peptide is 13 to 15 amino acids in size,
- the loss of binding observed with the UNK 6-17 and UNK 7-17 peptides suggests that the F residue at position 5 is the first residue for anchoring of the peptides in the binding site of the DP4 molecules (residue P1).

b) Determination of the Residues of the UNK1 Peptide which are Involved in Binding to the DP4 Molecules The results are given in table IX below:

TABLE IX

Loss of binding to DP401 and DP402 of the alanine and lysine mutants
(SEQ ID NOS: 14, 28 and 35-55, respectively, in order of appearance)

| PEPTIDE | 1 | 2 | 3 | 4 | 5 | 6 | 7 | 8 | 9 | 10 | 11 | 12 | 13 | 14 | 15 | 16 | 17 | DP*0401 | DP*0402 |
|---|---|---|---|---|---|---|---|---|---|---|---|---|---|---|---|---|---|---|---|
| UNK1 | E | K | K | Y | F | A | A | T | Q | F | E | P | L | A | A | R | L | 1 | 1.00 |
| UNK 3-15 | | | K | Y | F | A | A | T | Q | F | E | P | L | A | A | | | 1.5 | 1.7 |
| | | | | | P1 | | | | P4 | | P6 | | | P9 | | | | | | |
| UNK K3A | | | A | Y | F | A | A | T | Q | F | E | P | L | A | A | | | 0.9 | 1 |
| UNK Y4A | | | K | A | F | A | A | T | Q | F | E | P | L | A | A | | | 1.2 | 0.9 |
| UNK F5A | | | K | Y | A | A | A | T | Q | F | E | P | L | A | A | | | 41 | 5.7 |
| UNK T8A | | | K | Y | F | A | A | A | Q | F | E | P | L | A | A | | | 0.8 | 0.8 |
| UNK Q9A | | | K | Y | F | A | A | T | A | F | E | P | L | A | A | | | 0.8 | 0.6 |
| UNK F10A | | | K | Y | F | A | A | T | Q | A | E | P | L | A | A | | | 336 | 62 |
| UNK E11A | | | K | Y | F | A | A | T | Q | F | A | P | L | A | A | | | 0.5 | 0.5 |
| UNK P12A | | | K | Y | F | A | A | T | Q | F | E | A | L | A | A | | | 1.2 | 0.9 |
| UNK L13A | | | K | Y | F | A | A | T | Q | F | E | P | A | A | A | | | 3.1 | 2.3 |

TABLE IX-continued

Loss of binding to DP401 and DP402 of the alanine and lysine mutants
(SEQ ID NOS: 14, 28 and 35-55, respectively, in order of appearance)

| PEPTIDE | 1 | 2 | 3 | 4 | 5 | 6 | 7 | 8 | 9 | 10 | 11 | 12 | 13 | 14 | 15 | 16 | 17 | DP*0401 | DP*0402 |
|---|---|---|---|---|---|---|---|---|---|---|---|---|---|---|---|---|---|---|---|
| UNK Y4K | | | | K | K | F | A | A | T | Q | F | E | P | L | A | A | | 1.2 | 1 |
| UNK F5K | | | | K | Y | K | A | A | T | Q | F | E | P | L | A | A | | 569 | 297 |
| UNK A6K | | | | K | Y | F | K | A | T | Q | F | E | P | L | A | A | | 1.6 | 1 |
| UNK A7K | | | | K | Y | F | A | K | T | Q | F | E | P | L | A | A | | 2 | 1.2 |
| UNK T8K | | | | K | Y | F | A | A | K | Q | F | E | P | L | A | A | | 31 | 3.6 |
| UNK Q9K | | | | K | Y | F | A | A | T | K | F | E | P | L | A | A | | 1.6 | 0.9 |
| UNK F10K | | | | K | Y | F | A | A | T | Q | K | E | P | L | A | A | | 420 | 350 |
| UNK E11K | | | | K | Y | F | A | A | T | Q | F | K | P | L | A | A | | 1.3 | 0.7 |
| UNK P12K | | | | K | Y | F | A | A | T | Q | F | E | K | L | A | A | | 1.8 | 1.4 |
| UNK L13K | | | | K | Y | F | A | A | T | Q | F | E | P | K | A | A | | 81 | 70 |
| UNK A13K | | | | K | Y | F | A | A | T | Q | F | E | P | L | K | A | | 1.7 | 1.4 |
| UNK A15K | | | | K | Y | F | A | A | T | Q | F | E | P | L | A | K | | 1.7 | 1.4 |

The results show a loss of binding for F5A, F10A, F5K, F10K and L13K, which strongly suggests that the residues for anchoring of the peptides in the binding site of the DP4 molecules are, respectively, F5 at position P1, F10 at position P6 and L13 at position P9.

c) Determination of the DP401 Molecule-Binding and DP402 Molecule-Binding Units

The results are given in tables Xa and Xb and table XI below:

TABLE Xa

| Loss of binding to DP401 and DP402♣ of the mutants at P1, P4, P6 and P9 (SEQ ID NOS: 14, 28 and 56 to 81) | | | | | | | | | | | | | | | | | | | |
|---|---|---|---|---|---|---|---|---|---|---|---|---|---|---|---|---|---|---|---|
| PEPTIDE | 1 | 2 | 3 | 4 | 5 | 6 | 7 | 8 | 9 | 10 | 11 | 12 | 13 | 14 | 15 | 16 | 17 | DP*0401 | DP*0402 |
| UNK1 | E | K | K | Y | F | A | A | T | Q | F | E | P | L | A | A | R | L | 1.00 | 1.00 |
| UNK 3-15 | | | K | Y | F | A | A | T | Q | F | E | P | L | A | A | | | 1.4 | 1.4 |
| | | | | | P1 | | | P4 | | P6 | | | P9 | | | | | | |
| UNK F5Y | | | K | Y | Y | A | A | T | Q | F | E | P | L | A | A | | | 3 | 3.9 |
| UNK F5L | | | K | Y | L | A | A | T | Q | F | E | P | L | A | A | | | 3.6 | 6 |
| UNK F5E | | | K | Y | E | A | A | T | Q | F | E | P | L | A | A | | | 117 | 123 |
| UNK F5N | | | K | Y | N | A | A | T | Q | F | E | P | L | A | A | | | 398 | 76 |
| UNK F5T | | | K | Y | T | A | A | T | Q | F | E | P | L | A | A | | | 234 | 126 |
| UNK T8F | | | K | Y | F | A | A | F | Q | F | E | P | L | A | A | | | 2.7 | 1.7 |
| UNK T8L | | | K | Y | F | A | A | L | Q | F | E | P | L | A | A | | | 1.9 | 2.6 |
| UNK T8E | | | K | Y | F | A | A | E | Q | F | E | P | L | A | A | | | 2.7 | 3.7 |
| UNK T8D | | | K | Y | F | A | A | D | Q | F | E | P | L | A | A | | | 2 | 2.3 |
| UNK T8N | | | K | Y | F | A | A | N | Q | F | E | P | L | A | A | | | 4.1 | 4.8 |
| UNK T8Y | | | K | Y | F | A | A | Y | Q | F | E | P | L | A | A | | | 4.1 | 2.4 |
| UNK T8R | | | K | Y | F | A | A | R | Q | F | E | P | L | A | A | | | 17 | 6.7 |
| UNK T8S | | | K | Y | F | A | A | S | Q | F | E | P | L | A | A | | | 2.7 | 3.4 |
| UNK F10Y | | | K | Y | F | A | A | T | Q | Y | E | P | L | A | A | | | 2.4 | 3.4 |
| UNK F10L | | | K | Y | F | A | A | T | Q | L | E | P | L | A | A | | | 7.2 | 6.7 |
| UNK F10W | | | K | Y | F | A | A | T | Q | W | E | P | L | A | A | | | 2.2 | 2.5 |
| UNK F10E | | | K | Y | F | A | A | T | Q | E | E | P | L | A | A | | | 1405 | 1190 |
| UNK F10N | | | K | Y | F | A | A | T | Q | N | E | P | L | A | A | | | 2460 | 1809 |
| UNK F10T | | | K | Y | F | A | A | T | Q | T | E | P | L | A | A | | | 1171 | 476 |
| UNK L13F | | | K | Y | F | A | A | T | Q | F | E | P | F | A | A | | | 1.7 | 4 |
| UNK L13Y | | | K | Y | F | A | A | T | Q | F | E | P | Y | A | A | | | 2 | 15 |
| UNK L13E | | | K | Y | F | A | A | T | Q | F | E | P | E | A | A | | | 11 | 8 |
| UNK L13D | | | K | Y | F | A | A | T | Q | F | E | P | D | A | A | | | 9.4 | 9 |
| UNK L13N | | | K | Y | F | A | A | T | Q | F | E | P | N | A | A | | | 17 | 10 |
| UNK L13R | | | K | Y | F | A | A | T | Q | F | E | P | R | A | A | | | 64 | 43 |
| UNK L13V | | | K | Y | F | A | A | T | Q | F | E | P | V | A | A | | | 2.5 | 1.9 |

♣the values greater than 10 are indicated in bold

TABLE Xb

| Loss of binding to DP401 and DP402♣ of the mutants at P1, P4, P6 and P9 (SEQ ID NOS: 14 and 96 to 129) | | | | | | | | | | | | | | | | | | | |
|---|---|---|---|---|---|---|---|---|---|---|---|---|---|---|---|---|---|---|---|
| Peptides | 1 | 2 | 3 | 4 | 5 | 6 | 7 | 8 | 9 | 10 | 11 | 12 | 13 | 14 | 15 | 16 | 17 | | Loss |
| UNK | E | K | K | Y | F | A | A | T | Q | F | E | P | L | A | A | R | L | DP*0401 | DP*0402 |
| UNK F5D | | | K | Y | D | A | A | T | Q | F | E | P | L | A | A | | | 150 | 57 |
| UNK F5G | | | K | Y | G | A | A | T | Q | F | E | P | L | A | A | | | 160 | 55 |

TABLE Xb-continued

Loss of binding to DP401 and DP402♣ of the mutants at P1, P4, P6 and P9 (SEQ ID NOS: 14 and 96 to 129)

| Peptides | 1 | 2 | 3 | 4 | 5 | 6 | 7 | 8 | 9 | 10 | 11 | 12 | 13 | 14 | 15 | 16 | 17 | | Loss |
|---|---|---|---|---|---|---|---|---|---|---|---|---|---|---|---|---|---|---|---|
| UNK | E | K | K | Y | F | A | A | T | Q | F | E | P | L | A | A | R | L | DP*0401 | DP*0402 |
| UNK F5H | | | K | Y | H | A | A | T | Q | F | E | P | L | A | A | | | 150 | 36 |
| UNK F5I | | | K | Y | I | A | A | T | Q | F | E | P | L | A | A | | | 3 | 2 |
| UNK F5M | | | K | Y | M | A | A | T | Q | F | E | P | L | A | A | | | 3 | 3 |
| UNK F5P | | | K | Y | P | A | A | T | Q | F | E | P | L | A | A | | | 100 | 48 |
| UNK F5Q | | | K | Y | Q | A | A | T | Q | F | E | P | L | A | A | | | 260 | 97 |
| UNK F5R | | | K | Y | R | A | A | T | Q | F | E | P | L | A | A | | | 140 | 54 |
| UNK F5S | | | K | Y | S | A | A | T | Q | F | E | P | L | A | A | | | 160 | 42 |
| UNK F5V | | | K | Y | V | A | A | T | Q | F | E | P | L | A | A | | | 11 | 6 |
| UNK F5W | | | K | Y | W | A | A | T | Q | F | E | P | L | A | A | | | 0.5 | 1 |
| UNK T8G | | | K | Y | F | A | A | G | Q | F | E | P | L | A | A | | | 1 | 2 |
| UNK T8P | | | K | Y | F | A | A | P | Q | F | E | P | L | A | A | | | 3 | 2 |
| UNK T8H | | | K | Y | F | A | A | H | Q | F | E | P | L | A | A | | | 6 | 2 |
| UNK F10D | | | K | Y | F | A | A | T | Q | D | E | P | L | A | A | | | 2700 | 120 |
| UNK F10G | | | K | Y | F | A | A | T | Q | G | E | P | L | A | A | | | >7100 | 3700 |
| UNK F10H | | | K | Y | F | A | A | T | Q | H | E | P | L | A | A | | | 2400 | 220 |
| UNK F10I | | | K | Y | F | A | A | T | Q | I | E | P | L | A | A | | | 7 | 6 |
| UNK F10M | | | K | Y | F | A | A | T | Q | M | E | P | L | A | A | | | 4 | 1 |
| UNK F10P | | | K | Y | F | A | A | T | Q | P | E | P | L | A | A | | | 210 | 12 |
| UNK F10Q | | | K | Y | F | A | A | T | Q | Q | E | P | L | A | A | | | >7100 | 230 |
| UNK F10R | | | K | Y | F | A | A | T | Q | R | E | P | L | A | A | | | >7100 | 370 |
| UNK F10S | | | K | Y | F | A | A | T | Q | S | E | P | L | A | A | | | 500 | 33 |
| UNK F10V | | | K | Y | F | A | A | T | Q | V | E | P | L | A | A | | | 42 | 22 |
| UNK F10W | | | K | Y | F | A | A | T | Q | W | E | P | L | A | A | | | 1 | 1 |
| UNK F10C | | | K | Y | F | A | A | T | Q | C | E | P | L | A | A | | | 17 | 2 |
| UNK L13G | | | K | Y | F | A | A | T | Q | F | E | P | G | A | A | | | 15 | 12 |
| UNK L13H | | | K | Y | F | A | A | T | Q | F | E | P | H | A | A | | | 13 | 35 |
| UNK L13I | | | K | Y | F | A | A | T | Q | F | E | P | I | A | A | | | 1 | 3 |
| UNK L13P | | | K | Y | F | A | A | T | Q | F | E | P | P | A | A | | | 9 | 3 |
| UNK L13Q | | | K | Y | F | A | A | T | Q | F | E | P | Q | A | A | | | 8 | 2 |
| UNK L13S | | | K | Y | F | A | A | T | Q | F | E | P | S | A | A | | | 9 | 5 |
| UNK L13T | | | K | Y | F | A | A | T | Q | F | E | P | T | A | A | | | 5 | 3 |
| UNK L13W | | | K | Y | F | A | A | T | Q | F | E | P | W | A | A | | | 1 | 13 |

♣the values greater than 10 are indicated in bold

TABLE XI

Specificity of the DP4 molecule binding♣

| P1 | | P4 | | P6 | | P9 | |
|---|---|---|---|---|---|---|---|
| + | − | + | − | + | − | + | − |
| | | | DP*0401 | | | | |
| F, Y, L, I, M, W | H, T, S, A, G, P, K, R, D, E, N, Q, C, V | F, L, Y, H, T, A, S, G, P, I, M, Q, E, D, N, V, W, C | K,R | F, Y, L, W, I, M | H, V, A, G, T, P, S, K, R, E, D, N, Q, C | F, Y, V, A, I, P, W, L, M, Q, S, T, D | H, G, K, R, E, N, C |
| | | | DP*0402 | | | | |
| F, Y, L, A, I, M, V, W | H, T, S, G, P, K, R, D, E, N, Q, C | F, L, Y, H, T, A, S, G, P, I, MQ, E, D, N, V, | | F, Y, L, W, I, M, C | H, V, A, G, T, P, S, K, R, E, D, N, Q | F, V, A, I, P, L, M, C, Q, S, T, D, E | Y, H, W, G, K, R, N |

TABLE XI-continued

Specificity of the DP4 molecule binding♣

| P1 | | P4 | | P6 | | P9 | |
|---|---|---|---|---|---|---|---|
| + | − | + | − | + | − | + | − |
| | | K, W, C, R | | | | | |

♣The amino acids which caused, respectively, a loss of binding by a factor greater than 10 and less than 10 are indicated in the column (−) and the column (+); the anchoring residues are represented in bold and the differences between DPB1*0401 and DPB1*0402 are underlined.

The results obtained show that:

pockets P1, P6 and P9 of the binding site of the DP4 molecules accept aromatic or hydrophobic residues, pocket P4 of the binding site of the DP4 molecules is very permissive, as is, to a lesser extent, pocket P9, which also accepts Q, S, T and D residues, and the DPB1*0401 allele accepts a tyrosine or tryptophan residue at P9 but does not accept cysteine or glutamic acid residues at this position, nor alanine or valine residues at P1, nor lysine or arginine residues at P4, nor a cysteine residue at P6; the DPB1*0402 allele accepts an alanine or valine residue at P1, a lysine or arginine residue at P4, a cysteine residue at P6 and a cysteine or glutamic acid residue at P9, but does not accept a tyrosine or tryptophan residue at this position.

d) Identification of a Binding Unit in the Sequence of DP4-Ligand Peptides The binding activity of various DP4-ligand peptides was measured using the competition binding assay, under the conditions defined in table VI. The results are expressed by the $IC_{50}$ values (table XIII) or by the value of the ratio of the $IC_{50}$ values for the ligand peptide and for the UNK1 peptide (table XII).

The peptides tested, corresponding respectively to the following sequence SEQ ID NOS, are given in tables XII and XIII:

TT 947-963 (SEQ ID NO:20)
UNK1 9 (SEQ ID NO:14)
NY-ESO1 87-11, 119-143, 158-180, 166-180, (SEQ ID NO: 94,83,82,95),
UL21 283-302 (SEQ ID NO:18)
IL3 127-146 (SEQ ID NO:13)
NS-P2 (SEQ ID NO:4)
Api-ml 65-72, 69-86, 73-90, 77-94, 81-98 (SEQ ID NO:85, 88,89,17,86)
MAG 245-258 (SEQ ID NO:19)
MART1 1-20, 41-60, 51-73, 62-72, 103-118 (SEQ ID NO:90,91,87,92,93)

In parallel, the sequences of these DP4-ligand peptides were aligned and the presence of a DP4-binding unit as defined in table XI was sought (tables XII and XIII).

TABLE XII

Alignment of the sequences of the DP4-ligand peptides (SEQ ID NOS: 20, 14, 82, 18, 13, 4, 83, 83, 83, 84, 17, 17, 85, 19, 19, 86 and 87, respectively, in order or appearance)

| Peptides | Sequences P1  P6  P9 | 0401♣ | 0402♣ |
|---|---|---|---|
| TT947-963 | FNNFTVSFWLRVPKVSA | 0.57 | 0.75 |
| UNK1 | EKKYFAATQFEPLAARL | 1 | 1 |
| NY-ESO1 158-180 | LLMWITQCFLPVFLAQPPSGQRR | 2 | 7 |
| UL21 283-302 | RELWWVFYAGDRALEEPHAE | 2.86 | 2.78 |

TABLE XII-continued

Alignment of the sequences of the DP4-ligand peptides (SEQ ID NOS: 20, 14, 82, 18, 13, 4, 83, 83, 83, 84, 17, 17, 85, 19, 19, 86 and 87, respectively, in order or appearance)

| Peptides | Sequences P1  P6  P9 | 0401♣ | 0402♣ |
|---|---|---|---|
| IL3 127-146 | GPGAPADVQYDLYLNVANRR | 3.98 | 3.06 |
| NS-p2 | GVQIVRQIRSGERFLKIWSQ | 4.69 | 3.89 |
| NY-ESO1 119-143 | PGVLLKEFTVSGNILTIRLTAADHR | 12 | 12 |
| NY-ESO1 119-143 | PGVLLKEFTVSGNILTIRLTAADHR | 12 | 12 |
| NY-ESO1 119-143 | PGVLLKEFTVSGNILTIRLTAADHR | 12 | 12 |
| NY-ESO1 87-111 | LLEFYLAMPFATPMEAELARRSLAQ | 20 | 9 |
| Api ml 77-94 | TISSYFVGKMYFNLIDTK | 30 | 10 |
| Api ml 77-94 | TISSYFVGKMYFNLIDTK | 30 | 10 |
| Api ml 65-72 | DKFYDCLKNSADTSSYF | NT | 371.4 |
| MAG 245-258 | LLTQHFVQENYLEY | 30.2 | 38.89 |
| MAG 245-258 | LLTQHFVQENYLEY | 30.2 | 38.89 |
| Api ml 81-98 | YFVGKMYFNLIDTKCYKL | 150 | 70 |
| MART1 51-73 | RNGYRALMDKSLHVGTQCALTRR | 857 | 414 |

♣0401: relative DPB1*0401-binding activity of the peptides compared to the UNK1 peptide (binding activity equal to 1)
♣0402: relative DPB1*0402-binding activity of the peptides compared to the UNK1 peptide (binding activity equal to 1)

TABLE XIII

Binding of the Api ml, NY-ESO1 and MART1 peptides to DPB1*0401 and DPB*0402♣ (SEQ ID NOS: 14, 133, 88, 89, 17, 86, 90, 91, 134, 92-94, 83, 82, and 95, respectively, in order of appearance)

| peptides | Sequences | $IC_{50}$ (nM) 401 | 402 |
|---|---|---|---|
| UNK1 | EKKYFAATQFEPLAARL | 12 | 13 |
| Api ml 65-72 | DKFYDCLKNSADTISSYF | 50000 | 6500 |
| Api ml 69-86 | DCLKNSADTISSYFVGKM | >10000 | >10000 |
| Api ml 73-90 | NSADTISSYFVGKMYFNL | >10000 | >10000 |
| Api ml 77-94 | TISSYFVGKMYFNLIDTK | 450 | 175 |
| Api ml 81-98 | YFVGKMYFNLIDTKCYKL | 2250 | 1225 |
| MART1 1-20 | MPREDAHFIYGYPKKGHGHS | >10000 | >10000 |
| MART1 41-60 | LLIGCWYCRRRNGYRALMDK | >10000 | >10000 |

TABLE XIII-continued

Binding of the Api m1, NY-ESO1 and MART1 peptides to DPB1*0401 and DPB*0402* (SEQ ID NOS: 14, 133, 88, 89, 17, 86, 90, 91, 134, 92-94, 83, 82, and 95, respectively, in order or appearance)

| peptides | Sequences | IC$_{50}$ (nM) 401 | 402 |
|---|---|---|---|
| MART1 51-73** | RRNGYRALMDKSLHVGTQCALTRR | 8000 | 4000 |
| MART1 62-72 | LMDKSLHVGTQCALTRRCPQ | >10000 | >10000 |
| MART1 103-118 | AYEKLSAEQSPPPYSP | >10000 | >10000 |
| NY-ESO1 87-111 | LLEFYLAMPFATPMEAELARRSLAQ | 183 | 83 |
| NY-ESO1 119-143*** | PGVLLKEFTVSGNILTIRLTAADHR | 110 | 117 |
| NY-ESO1 158-180 | LLMWITQCFLPVFLAQPPSGQRR | 20 | 67 |
| NY-ESO1 166-180 | FLPVFLAQPPSGQRR | >10000 | >10000 |

*The amino acids compatible with the unit for binding to the DPB1*0401 and DPB1*0402 alleles are indicated in bold and the complete binding units are underlined.
**The sequence of this peptide is described in Zarour et al., PNAS, 2000, 97, 400-405.
***The sequence of this peptide is described in Zarour et al., Cancer Res., 2000, 60, 4646-4952.

The results show that, for most of the DP4-ligand peptides, a strong correlation exists between the presence of at least two residues P1 and P6 or P6 and P9 as defined in table XI and a high affinity for the DP4 molecules (IC$_{50}$<1000 nM). These results also show that the most important residues in the binding to HLA-DP4 are the aromatic or hydrophobic residues at position P1 and P6; these same residues at position P9 are less important.

EXAMPLE 6

Prediction of the Sequence of HLA-DP4-Ligand Peptides Based on an Amino Acid Sequence 1) Materials and Methods An HLA-DP4 molecule-binding matrix was established based on the binding activities (IC$_{50}$) of the mutants of the UNK 3-15 peptide, measured using the assay for binding to the DP4 molecules encoded by the DPB1*0401 and DPB1*0402 alleles, as defined above, using the UNK 3-15 peptide as tracer peptide (example 5 and tables IX, Xa, Xb and XI). The contribution of each of the amino acids at positions P1, P4, P6 and P9 of said mutant peptides to the binding to the DP*0401 and DP*0402 molecules is evaluated by a binding score corresponding to the logarithm (log) of the ratio of the IC$_{50}$ values for the mutant peptide and for the UNK 3-15 peptide. The score for binding to the DP*0401 and DP*0402 molecules, obtained for each of the amino acids at positions P1, P4, P6 and P9 of said mutant peptides, constitutes the HLA-DP4-binding matrix shown in table XIV below:

TABLE XIV

| HLA-DP4-binding matrix | | | | | | | | | | | | |
|---|---|---|---|---|---|---|---|---|---|---|---|---|
| | | Amino acid | | | | | | | | | | |
| DP4 | Position | A | D | E | F | G | H | I | K | L | M | N |
| DP*0401 | P1 | 1.6 | 1.7 | 1.85 | 0 | 2.2 | 2.17 | 0.48 | 2.6 | 0.48 | 0.48 | 2.32 |
| | P4 | 0 | 0.3 | 0.3 | 0.3 | 0 | 0.78 | 0.3 | 1.48 | 0.3 | 0.3 | 0.6 |
| | P6 | 2.38 | 3.32 | 2.9 | 0 | 3.85 | 3.4 | 0.85 | 2.43 | 0.78 | 0.6 | 3.15 |
| | P9 | 0.6 | 0.85 | 1.04 | 0 | 1.18 | 1.11 | 0 | 1.85 | 0 | 0 | 1.15 |
| DP*0402 | P1 | 0.85 | 1.76 | 1.85 | 0 | 1.76 | 1.56 | 0.3 | 2.28 | 0.48 | 0.48 | 1.78 |
| | P4 | 0 | 0.3 | 0.48 | 0 | 0 | 0.3 | 0.3 | 0.7 | 0.3 | 0.3 | 0.6 |
| | P6 | 1.88 | 3.85 | 2.9 | 0 | 3.57 | 2.33 | 0.78 | 2.28 | 0.7 | 0 | 3.08 |
| | P9 | 0.6 | 0.9 | 0.9 | 0.7 | 1.08 | 1.54 | 0.48 | 1.9 | 0 | 0.3 | 0.85 |

| | | Amino acid | | | | | | | |
|---|---|---|---|---|---|---|---|---|---|
| DP4 | Position | P | Q | R | S | T | V | W | Y | C |
| DP*0401 | P1 | 1.98 | 2.41 | 2.14 | 2.2 | 2.15 | 1.04 | 0 | 0.48 | 2.32 |
| | P4 | 0.48 | 0.3 | 1.5 | 0.3 | 0 | 0.15 | 0.3 | 0.6 | 0.6 |

TABLE XIV-continued

HLA-DP4-binding matrix

|  |  |  |  |  |  |  |  |  |  |  |
|---|---|---|---|---|---|---|---|---|---|---|
|  | P6 | 2.32 | 3.85 | 3.85 | 2.7 | 2.85 | 1.62 | 0.3 | 0.3 | 1.23 |
|  | P9 | 0.95 | 0.9 | 1.7 | 0.95 | 0.6 | 0.3 | 0 | 0.3 | 1.15 |
| DP*0402 | P1 | 1.68 | 1.99 | 1.72 | 1.62 | 1.85 | 0.78 | 0 | 0.48 | 1.78 |
|  | P4 | 0.3 | 0.3 | 0.7 | 0.48 | 0 | 0.15 | 0 | 0 | 0.6 |
|  | P6 | 1.08 | 2.36 | 2.57 | 1.52 | 2.48 | 1.34 | 0.3 | 0.48 | 0.3 |
|  | P9 | 0.48 | 0.3 | 1.6 | 0.7 | 0.6 | 0.3 | 1.11 | 1.18 | 0.85 |

Starting with an amino acid sequence, the binding of the peptides of at least 9 amino acids included in said sequence is calculated, based on the matrix above, by adding, for each fragment of 9 amino acids of said peptide, for example overlapping fragments of 9 amino acids covering this entire sequence, the binding scores for the residues at positions 1, 4, 6 and 9 of said fragment.

Peptides having binding scores of, respectively, 0, 1, 2, 3 and 4 correspond to peptides which exhibit a 1-, 10-, 100-, 1000- and 10 000-fold loss of binding relative to the UNK 3-15 peptide ($IC_{50}$ 10 nM), i.e. exhibiting an estimated binding activity of, respectively, 10 nM, 100 nM, 1000 nM, 10 μM and 100 μM.

The peptides having the lowest binding scores, preferably less than 2, preferably less than 1, even more preferably close to 0, are selected; these peptides correspond to those for which the HLA-DP4-binding activity, estimated based on the binding matrix as defined above, is the highest.

2) Results

The correlation between the binding score for the peptides (estimated using the HLA-DP4-binding matrix, table XIV), and their affinity for the HLA-DP4 molecules (residues in the binding assay as defined above) was analyzed for 44 peptides studied in examples 4 and 5.

The results are given in table XV and FIG. 2.

TABLE XV

Binding score and HLA-DP4-binding activity of various peptides

|  | DP*0401 | | DP*0402 | |
|---|---|---|---|---|
| Peptide | $IC_{50}$ (nM) | Binding score | $IC_{50}$ (nM) | Binding score |
| TT947-963 | 4.61 | 0.90 | 7 | 1.08 |
| UNK 1 | 9.47 | 0.00 | 10.00 | 0.00 |
| NY-ESO1 158-180 | 30.00 | 0.60 | 70.00 | 0.60 |
| UL21 283-302 | 22.89 | 1.77 | 20.00 | 2.01 |
| IL3 127-146 | 30.37 | 1.94 | 30.00 | 1.86 |
| NSP2 | 40.00 | 2.44 | 40.00 | 2.69 |
| NY-ESO1 119-143 | 100.00 | 2.16 | 100.00 | 1.90 |
| NY-ESO1 87-11 | 186.12 | 1.73 | 87.00 | 1.26 |
| MAG 245-258 | 250.00 | 0.90 | 400.00 | 1.68 |
| MART1 51-73 | 8000.00 | 3.76 | 4000.00 | 2.45 |
| Api-m1 1-18 | 10000.00 | 1.89 | 10000.00 | 2.08 |
| Api-m1 5-22 | 10000.00 | 4.88 | 10000.00 | 3.33 |
| Api-m1 9-26 | 10000.00 | 3.58 | 10000.00 | 3.33 |
| Api-m1 13-30 | 10000.00 | 2.92 | 10000.00 | 2.38 |

TABLE XV-continued

Binding score and HLA-DP4-binding activity of various peptides

|  | DP*0401 | | DP*0402 | |
|---|---|---|---|---|
| Peptide | $IC_{50}$ (nM) | Binding score | $IC_{50}$ (nM) | Binding score |
| Api-m1 17-34 | 10000.00 | 2.92 | 10000.00 | 2.38 |
| Api-m1 21-38 | 10000.00 | 4.08 | 10000.00 | 3.40 |
| Api-m1 25-42 | 10000.00 | 3.97 | 10000.00 | 2.64 |
| Api-m1 29-46 | 10000.00 | 2.56 | 10000.00 | 1.86 |
| Api-m1 33-50 | 10000.00 | 2.56 | 10000.00 | 1.86 |
| Api-m1 37-54 | 10000.00 | 4.00 | 10000.00 | 3.07 |
| Api-m1 41-58 | 10000.00 | 4.00 | 10000.00 | 3.07 |
| Api-m1 45-62 | 10000.00 | 3.23 | 10000.00 | 2.45 |
| Api-m1 49-66 | 10000.00 | 3.23 | 10000.00 | 2.45 |
| Api-m1 53-70 | 10000.00 | 3.15 | 10000.00 | 2.45 |
| Api-m1 57-74 | 10000.00 | 3.15 | 10000.00 | 2.90 |
| Api-m1 61-78 | 10000.00 | 3.15 | 10000.00 | 2.90 |
| Api-m1 65-82 | 50000.00 | 3.64 | 6500.00 | 2.90 |
| Api-m1 69-86 | 10000.00 | 2.70 | 10000.00 | 1.94 |
| Api-m1 73-90 | 10000.00 | 1.78 | 10000.00 | 1.18 |
| Api-m1 77-94 | 450 | 1.34 | 175.00 | 1.18 |
| Api-m1 81-98 | 2250 | 1.34 | 1225.00 | 0.78 |
| Api-m1 85-102 | 10000.00 | 1.71 | 10000.00 | 0.78 |
| Api-m1 89-106 | 10000.00 | 1.71 | 10000.00 | 0.78 |
| Api-m1 93-110 | 10000.00 | 4.27 | 10000.00 | 3.02 |
| Api-m1 97-114 | 10000.00 | 4.98 | 10000.00 | 3.46 |
| Api-m1 101-118 | 10000.00 | 3.67 | 10000.00 | 3.21 |
| Api-m1 105-122 | 10000.00 | 3.65 | 10000.00 | 3.21 |
| Api-m1 109-126 | 10000.00 | 3.65 | 10000.00 | 3.44 |
| Api-m1 113-130 | 10000.00 | 3.96 | 10000.00 | 3.50 |
| Api-m1 117-134 | 10000.00 | 1.86 | 10000.00 | 1.98 |
| MART1 1-20 | 10000.00 | 3.16 | 10000.00 | 2.16 |
| MART1 41-60 | 10000.00 | 2.48 | 10000.00 | 2.20 |
| MART1 62-72 | 10000.00 | 4.00 | 10000.00 | 2.46 |
| MART1 103-118 | 10000.00 | 4.11 | 10000.00 | 2.95 |

These results show that a strong correlation exists -between the binding score and the affinity of the peptides for HLA-DP4. Specifically, taking as activity threshold a binding score <2 and a binding activity $IC_{50}$<1000 nM:

80% of the peptides having a binding score <2 for the HLA-DP4 molecules (DP*0401 and DP*0402) exhibit a high affinity for these molecules ($IC_{50}$<1000 nM, true positive peptides), and 82% and 76% of the peptides having a binding score ≧2 for the HLA-DP4 molecules (respectively DP*0401 and DP*0402) exhibit a low affinity for these molecules ($IC_{50}$≧1000 nM, true negative peptides)

Consequently, the HLA-DP4-binding matrix can be used to predict the sequence of HLA-DP4-ligand peptides from any amino acid sequence, in particular a sequence representing an antigen of interest.

The invention claimed is:

1. A method of selecting at least one test molecule that binds to HLA-DP4, comprising:

(i) incubating purified HLA-DP4 in the presence of a labeled peptide and various concentrations of at least one test molecule thereby forming a HLA-DP4/labeled peptide complex and at least one HLA-DP4/test molecule complex, wherein the labeled peptide contains a label and the peptide consists of an amino acid sequence of:

SEQ ID NO: 4 or a fragment of SEQ ID NO: 4 which includes at least positions 10 to 18 of SEQ ID NO: 4, SEQ ID NO: 9 or a fragment of SEQ ID NO: 9 which includes at least positions 4 to 12 of SEQ ID NO: 9, SEQ ID NO: 12 or a fragment of SEQ ID NO: 12 which includes at least positions 3 to 11 of SEQ ID NO: 12, SEQ ID NO: 13 or a fragment of SEQ ID NO: 13 which includes at least positions 8 to 16 of SEQ ID NO: 13, SEQ ID NO: 14 or a fragment of SEQ ID NO: 14 which includes at least positions 5 to 13 of SEQ ID NO: 14, SEQ ID NO: 18 or a fragment of SEQ ID NO: 18 which includes at least positions 3 to 11 of SEQ ID NO: 18, or SEQ ID NO: 19 or a fragment of SEQ ID NO: 19 which includes at least positions 6 to 14 or 2 to 10 of SEQ ID NO: 19;

(ii) separating the HLA-DP4/labeled peptide complex and the at least one HLA-DP4/test molecule complex formed;

(iii) detecting the at least one HLA-DP4/labeled peptide complex by measuring a signal associated with the labeled peptide; and (iv) selecting at least one test molecule that exhibits a binding activity $IC_{50}<1,000$ nM, which corresponds to the concentration of the at least one test molecule that inhibits 50% of the competitive HLA-DP4 binding of the labeled peptide.

2. The method according to claim 1, wherein the at least one test molecule is a peptide selected from a library of overlapping peptides covering a sequence of an antigen.

3. The method according to claim 1, wherein the at least one test molecule is selected from the group consisting of at least one synthetic peptide molecule, pseudopeptide, antigenic T-epitope peptide, modified peptide, lipopeptide, and glycopeptides.

4. The method according to claim 1, wherein the at least one test molecule exhibits a binding activity of $IC_{50}=100$ nM, which corresponds to the concentration of the at least one test moleculel that inhibits 50% of the competitive binding of the labeled peptide.

5. The method according to claim 1, wherein the at least one test molecule exhibits a binding activity of $IC_{50}=10$ nM, which corresponds to the concentration of the at least one test molecule that inhibits 50% of the competitive binding of the labeled peptide.

6. The method according to claim 1, wherein the purified HLA-DP4 is encoded by DPA1*103/DPB1*0401 alleles or DPA1*103/DPB1*0402 alleles.

7. The method according to claim 1, wherein the labeled peptide is selected from the group consisting of a biotinylated peptide, a radiolabeled peptide and a peptide coupled to a fluorochrome.

8. The method according to claim 1, wherein the labeled peptide incubated with purified HLA-DP4 is at a concentration of <200 nM.

9. The method according to claim 1, wherein the labeled peptide incubated with purified HLA-DP4 is at a concentration of <20 nM.

10. The method according to claim 1, wherein the labeled peptide incubated with purified HLA-DP4 is at a concentration of <10 nM.

11. The method according to claim 1, wherein (i) constitutes incubating purified HLA-DP4 in the presence of a labeled peptide and various concentrations of a test molecule thereby forming a HLA-DP4/labeled peptide complex and a HLA-DP4/test molecule complex.

12. The method according to claim 1, wherein the at least one labeled peptide is selected from the group consisting of: SEQ ID NO: 4, SEQ ID NO: 9, SEQ ID NO: 12, SEQ ID NO: 13, SEQ ID NO: 14, SEQ ID NO: 18 and SEQ ID NO: 19.

* * * * *

UNITED STATES PATENT AND TRADEMARK OFFICE
CERTIFICATE OF CORRECTION

| | | |
|---|---|---|
| PATENT NO. | : 7,718,575 B2 | Page 1 of 1 |
| APPLICATION NO. | : 10/491891 | |
| DATED | : May 18, 2010 | |
| INVENTOR(S) | : Bernard Maillere et al. | |

It is certified that error appears in the above-identified patent and that said Letters Patent is hereby corrected as shown below:

On the title page, Item (73), the Assignee information is incorrect. Item (73) should read:

-- (73) Assignee: Commissariat a l'Energie Atomique, Paris (FR) --

Signed and Sealed this
Twenty-ninth Day of March, 2011

David J. Kappos
*Director of the United States Patent and Trademark Office*